(12) United States Patent
Mousa et al.

(10) Patent No.: US 9,851,365 B2
(45) Date of Patent: Dec. 26, 2017

(54) DIGITAL MICROFLUIDIC LIQUID-LIQUID EXTRACTION DEVICE AND METHOD OF USE THEREOF

(75) Inventors: Noha Ahmed Mousa, Assiut (EG); Mais J. Jebrail, Richmond Hill (CA); Mohamed Omar Abdelgawad, Assiut (EG); Aaron R. Wheeler, Toronto (CA); Robert Fredric Joseph Casper, Toronto (CA)

(73) Assignee: THE GOVERNING COUNCIL OF THE UNIVERSITY OF TORONTO, Toronto, Ontario (CA)

(*) Notice: Subject to any disclaimer, the term of this patent is extended or adjusted under 35 U.S.C. 154(b) by 1305 days.

(21) Appl. No.: 13/203,701

(22) PCT Filed: Feb. 26, 2010

(86) PCT No.: PCT/CA2010/000276
§ 371 (c)(1),
(2), (4) Date: Dec. 6, 2011

(87) PCT Pub. No.: WO2010/096928
PCT Pub. Date: Sep. 2, 2010

(65) Prior Publication Data
US 2012/0085645 A1    Apr. 12, 2012

Related U.S. Application Data

(63) Continuation-in-part of application No. 12/379,704, filed on Feb. 26, 2009, now Pat. No. 8,202,736.

(51) Int. Cl.
*G01N 33/536* (2006.01)
*G01N 33/74* (2006.01)
*B01L 3/00* (2006.01)
*G01N 1/40* (2006.01)

(52) U.S. Cl.
CPC ........ *G01N 33/74* (2013.01); *B01L 3/502761* (2013.01); *B01L 3/502784* (2013.01); *G01N 1/4055* (2013.01); *B01L 2300/087* (2013.01); *B01L 2300/089* (2013.01); *B01L 2400/0415* (2013.01); *G01N 2001/4061* (2013.01)

(58) Field of Classification Search
CPC ........ B01L 3/502761; B01L 3/502784; B01L 2300/087; B01L 2300/089; B01L 2400/0415; G01N 1/405; G01N 33/07; G01N 2001/4061
See application file for complete search history.

(56) References Cited

U.S. PATENT DOCUMENTS

| | | |
|---|---|---|
| 4,569,575 A | 2/1986 | Le Pesant et al. |
| 4,636,785 A | 1/1987 | Le Pesant |
| 4,818,052 A | 4/1989 | Le Pesant et al. |
| 5,486,337 A | 1/1996 | Ohkawa |
| 6,352,838 B1 | 5/2002 | Krulevitch et al. |
| 6,565,727 B1 | 5/2003 | Shenderov |
| 6,773,566 B2 | 8/2004 | Shenderov |
| 6,911,132 B2 | 6/2005 | Pamula et al. |
| 6,989,234 B2 | 1/2006 | Kolar et al. |
| 7,147,763 B2 | 10/2006 | Elrod et al. |
| 7,163,612 B2 | 1/2007 | Sterling et al. |
| 7,214,302 B1 | 8/2007 | Reihs et al. |
| 7,255,780 B2 | 8/2007 | Shendervo |
| 7,328,979 B2 | 2/2008 | Decre et al. |
| 7,329,545 B2 | 2/2008 | Pamula et al. |
| 2004/0171169 A1 | 9/2004 | Kallury et al. |
| 2004/0211659 A1 | 10/2004 | Velev |
| 2005/0115836 A1 | 6/2005 | Reihs |
| 2005/0148091 A1 | 7/2005 | Kitaguchi et al. |
| 2005/0191759 A1 | 9/2005 | Pedersen-Bjergaard et al. |
| 2006/0231398 A1* | 10/2006 | Sarrut et al. ............... 204/450 |
| 2007/0023292 A1 | 2/2007 | Kim et al. |
| 2007/0148763 A1 | 6/2007 | Huh et al. |

(Continued)

FOREIGN PATENT DOCUMENTS

| | | |
|---|---|---|
| WO | 2007120241 | 10/2007 |
| WO | 2007136386 | 11/2007 |

(Continued)

OTHER PUBLICATIONS

Vijay Srinivasan, Vamsee K. Pamular and Richard B. Fair, "An integrated digital microfluidic lab-on-a-chip for clinical diagnostics on human physiological fluids", Lab Chip, 2004, 4, 310-315.*
Chatterjee et al. Droplet-based microfluidics with nonaqueous solvents and solutions. Lab Chip. 2006, 6, pp. 199-206.
Jebrail et al. Digital Microfluidic Method for Protein Extraction by Precipitation. Analytical Chemistry. vol. 81, No. 1, 1, 2009. Jan.
Moon et al. An integrated digital microfluidic chip for multiplexed proteomic sample preparation and analysis by Lab Chip. 2006, 6, pp. 199-206. Maldi-Ms.
Shih-Kang Fan. Cross-scale electric manipulations of cells and droplets by frequency-modulated dielectrophoresis and electrowetting. The Royal Society of Chemistry (2008), Lab Chip vol. 8, pp. 1325-1331.

(Continued)

*Primary Examiner* — Ann Lam
(74) *Attorney, Agent, or Firm* — Shay Glenn LLP

(57) ABSTRACT

Methods and devices for liquid-liquid extraction using digital microfluidic arrays are provided. A polar droplet is transported to a separation region containing a substantially non-polar solvent, where non-polar impurities may be extracted from the polar droplet while maintaining a distinct phase separation. In a preferred embodiment, biological samples containing hormones are dried on a digital microfluidic array, lysed by a lysing solvent, dried, subsequently dissolved in a polar solvent, and further purified in a separation step in which droplets are transported through a volume of non-polar solvent. The method disclosed herein provides the distinct advantage of an automated sample preparation method that is capable of extracting hormones from low sample volumes with high precision and recovery.

43 Claims, 11 Drawing Sheets

(56) References Cited

U.S. PATENT DOCUMENTS

| | | |
|---|---|---|
| 2007/0242111 A1 | 10/2007 | Pamula et al. |
| 2008/0044914 A1 | 2/2008 | Pamula et al. |
| 2008/0156983 A1 | 7/2008 | Fourrier et al. |
| 2008/0185339 A1 | 8/2008 | Delapierre et al. |
| 2009/0203063 A1 | 8/2009 | Wheeler et al. |
| 2010/0081578 A1 | 4/2010 | Wheeler et al. |
| 2010/0087633 A1 | 4/2010 | Wheeler et al. |
| 2010/0213074 A1 | 8/2010 | Mousa et al. |
| 2010/0311599 A1 | 10/2010 | Wheeler et al. |

FOREIGN PATENT DOCUMENTS

| | | |
|---|---|---|
| WO | 2008051310 | 5/2008 |
| WO | 2010040227 | 4/2010 |

OTHER PUBLICATIONS

Ting-Hsuan Chen. Selective Wettability Assisted Nanoliter Sample Generation Via Electrowetting-Based Transportation. Proceedings of the Fifth International Conference on Nanochannels, Microchannels and Minichannels (ICNMM) (Jun. 18-20, 2007).

Hongmei Yu. A plate reader-compatible microchannel array for cell biology assays. The Royal Society of Chemistry (2007) Lab Chip vol. 7, pp. 388-391.

Marc A. Unger. Monolithic Microfabricated Valves and Pumps by Multilayer Soft Lithography. Science (2000) vol. 288.

A.S. Verkman. Drug Discovery in Academia. Am J Physiol Cell Physiol (2004) vol. 286, pp. 465-474.

Jamil El-Ali. Cells on chips. Nature (2006) Insight Review. vol. 442.

Darren R. Link. Electric Control of Droplets in Microfluidic Devices. Communications. Angew Chem. Int (2006) vol. 45 pp. 2556-2560.

Wheeler Aaron A. Electrowetting-Based Microfluidics for Analysis of Peptides and Proteins by Matrix-Assisted Laser Desorption/Ionization Mass Spectrometry. (Aug. 2004) Anal Chem. vol. 76, No. 16.

Eun Zoo Lee. Removal of bovine serum albumin using solid-phase extraction with in-situ polymerized stationary phase in a microfluidic device. ScienceDirect. Journal of Chromatography A. (2008) vol. 1187. pp. 11-17.

Hsih Yin Tan. A lab-on-a-chip for detection of nerve agent sarin in blood. The Royal Society of Chemistry (2008). Lab Chip vol. 8. pp. 885-891.

Kai-Cheng Chuang. Direct Handwriting Manipulation of Droplets by Self-Aligned Mirror-EWOD Across a Dielectric Sheet. MEMS (Jan. 2006) pp. 22-26.

Mohamed Abdelgawad. Low-cost, rapid-prototyping of digital microfluidics devices. Springer. Microfluid Nanofluid (2008) vol. 4. pp. 349-355.

Eric Lebrasseur. Two-dimensional electrostatic actuation of droplets using a single electrode panel and development of disposable plastic film card. ScienceDirect. Sensors and Actuators (2007) vol. 136. pp. 358-366.

* cited by examiner

DIGITAL MICROFLUIDIC LIQUID-LIQUID EXTRACTION DEVICE AND METHOD OF USE THEREOF

This application is a national phase application under 35 USC 371 of International Patent Application No. PCT/CA2010/000276, filed Feb. 26, 2010, and titled "Digital Microfluidic Liquid-Liquid Extraction Device and Method of Use Thereof," which is a continuation of U.S. patent application Ser. No. 12/379,704, filed on Feb. 26, 2009, titled "Method of Hormone Extraction Using Digital Microfluidics," the entire contents of which are incorporated herein by reference.

FIELD OF THE INVENTION

The present invention relates to a method of the extraction and purification of liquids using digital microfluidics. More particularly, the invention relates to the extraction and purification of hormones using digital microfluidics.

BACKGROUND OF THE INVENTION

Hormones are chemical messengers that transport a signal from one cell to another. They play important roles in regulation of physiological activities. The effects of hormones include stimulation or inhibition of growth, regulating metabolism, induction or suppression of programmed cell death, and controlling the reproductive cycle, just to name a few. Thus, there are a wide range of clinical conditions that require frequent monitoring of hormones in biological samples, such as blood or tissue, for proper diagnosis and treatment of physiological disorders associated with the hormones.

For example, sex steroids are steroid hormones which are fundamental for growth and reproduction, and disturbances in their physiological levels can cause a multitude of clinical disorders, including growth retardation, infertility, or hormone-sensitive cancers (e.g., breast, endometrial and prostate cancers) [1-4]. Moreover, exogenous sex steroids have been used for decades as contraceptives, hormone replacements, and fertility and anti-cancer therapies [5-9]. Estrogen is a steroidal sex hormone of fundamental importance for normal human growth, reproduction and in breast cancer development and progression.

Diagnostic assays for the measurement of sex steroids are of central importance to the management of a wide range of clinical conditions and also play a key role in many areas of epidemiological study. Many clinical applications, such as the monitoring of blood levels of estradiol and other hormones in women undergoing treatment for infertility, have spurred the development of highly automated and cost-effective immunoassays.

Unfortunately, modern immunoassays often lack the low limit of detection required for some clinical areas, including monitoring menopausal women, patients on anti-estrogen therapies [10], or children [11-13]. Indeed, these clinical segments often present cases where the required assay dynamic range falls below the practical detection limits of commercial assays. This lack of performance in commercial assays has been demonstrated in studies of multiple automated analyzers, where considerable variability has been observed in results for samples with low concentrations. This failure of modern automated assays for sex steroids to address the clinical requirements in patient segments presenting low concentrations has prompted the Endocrinology Society to issue a statement cautioning against the use of standard assays for low level testosterone measurements. In recent years, a consensus has emerged that mass spectroscopy provides the optimal performance for low level steroid measurement.

Despite the widespread acknowledgement of the utility of mass spectroscopy as a preferred diagnostic tool low level steroid measurements, one of the key problems that limits its practical performance is sample preparation. Assays for steroids in clinical samples often require extensive pre-processing to extract the analytes from the matrix (i.e., unwanted chemical constituents and insoluble tissue debris). This is the case for all tissue samples, whole blood, and plasma and for any samples (including serum) that are to be evaluated by mass spectrometry or indirect immunoassays. Moreover, such processing techniques are known to be especially important for accurate quantification in subjects with low hormone levels. Unfortunately, sample processing techniques for analysis of steroids (including lysis, homogenization, extraction, and resolubilization) are labor-intensive (wasting many hours of laboratory time [14, 15]), and are thus prone to human error. Furthermore, assays often require hundreds of milligrams of tissue [16, 17] or milliliters of blood [18], which is ill-suited for routine clinical testing.

One promising technology for improved sample preparation is digital microfluidics. Digital microfluidics is a new technology in which discrete unit droplets are manipulated in air on the open surface of an array of electrodes by applying voltages to the electrodes [19]. Sample and reagent droplets with volumes of less than one microliter can be moved in multiple and reconfigurable paths defined by the actuation sequence of an array of electrodes. The mechanism for fluid motion depends on a host of factors and may be due to electrowetting or dielectrophoresis. Unlike conventional microfluidics, digital microfluidics enables the transport, mixing, merging and dispensing from reservoirs of single isolated droplets. The technology has been demonstrated for diverse applications including cell based assays, enzyme assays, protein profiling, and polymerase chain reaction [41].

Digital microfluidic arrays are typically made by depositing an array of electrodes onto a first planar surface and subsequently coating the surface with a layer of a hydrophobic insulator such as Teflon-AF. Electrical contact pads are connected to the electrodes, enabling the electrodes to be individually addressed. Sample and reagent reservoirs are incorporated into the array by including electrodes capable of supporting more than one unit droplet of fluid. Unit droplets can be extracted from reservoirs by actuating electrodes adjacent to the reservoir.

In a closed digital microfluidic array, a second planar surface, onto which a single planar electrode is typically deposited and subsequently coated with a layer of a hydrophobic insulator, is placed parallel to the first planar surface, forming a planar air gap. Accordingly, droplets are sandwiched between the two surfaces. Fluid droplets placed on the array elements (i.e. on the insulating layer directly above an array electrode) can be made to move by applying a voltage between an array electrode and the single planar electrode. Alternatively, an open digital microfluidic array can be formed with the first surface alone, where droplets are moved by applying a voltage between neighbouring electrodes.

While digital microfluidic systems have been successfully developed for a wide range of practical uses, the prior art has not provided a method of adapting their use to the efficient extraction of sex steroids or other hormones from biological samples. Thus, there is a need for a fast, economical and reliable method for analysis of hormone extraction and analysis in biological samples using digital microfluidics.

SUMMARY OF THE INVENTION

The aforementioned need is addressed herein by providing devices and methods for liquid-liquid extraction using digital microfluidic arrays. In a first embodiment, a polar droplet is transported to a separation region of a digital microfluidic device, where a substantially non-polar solvent is retained over an extraction portion of the digital microfluidic array. By transporting a droplet of a polar liquid to the separation region, non-polar impurities may be extracted from the polar droplet while maintaining a distinct phase separation.

Accordingly, in a first aspect of the invention, a method is provided of separating a non-polar species from a substantially polar droplet using a digital microfluidic device, the device comprising an input array, a separation array in flow communication with the input array, and an output array in flow communication with the separation array, wherein the input array, the separation array and the output array each comprise at least one digital microfluidic element, the device further comprising a substantially non-polar liquid retained over the separation array, the method comprising the steps of:

actuating the device to transport the droplet from the input array to the separation array, wherein the species is extracted from the droplet while maintaining the droplet as a distinct liquid phase within the substantially non-polar liquid; and actuating the device to transport the droplet from the separation array to the output array.

In another aspect of the invention, a digital microfluidic device is provided for the separation of a non-polar species from a substantial polar droplet to a substantially non-polar liquid, the device comprising:

a substrate;

an input array comprising at least one digital microfluidic element formed on the substrate;

a separation array in flow communication with the input array, the separation array comprising at least one digital microfluidic element formed on the substrate;

a retaining means for retaining a substantially non-polar liquid over the separation array, wherein the droplet may be transported among elements of the separation array and within the non-polar liquid while maintaining a separate liquid phase, and wherein the species may be extracted from the droplet into the substantially non-polar liquid while transporting the droplet;

an output array in flow communication with the separation array, the output array comprising at least one digital microfluidic element formed on the substrate; and contact means for individually electrically addressing the digital microfluidic elements.

In a preferred embodiment, the retaining means comprises a wall means, said wall means surrounding a portion of said separation array, wherein said wall means does not interrupt the path of said droplet as it is transported to and from said separation array. In one embodiment, the wall means may comprise a raised portion of the substrate, or a raised portion of photoresist.

In another aspect of the invention, there is provided a method for the extraction of hormones from biological samples using a digital microfluidic array. The method is performed by drying biological samples containing hormones on a digital microfluidic array, lysing the sample with a lysing solvent, drying the lysate, subsequently dissolving the lysate in a polar solvent, and further purifying the polar solution in a separation step in which droplets are transported through a volume of non-polar solvent.

Accordingly, an embodiment of the invention provides a method of extracting a hormone from a biological sample using a digital microfluidic device, the device comprising an input array, a separation array in flow communication with the input array, and an output array in flow communication with the separation array, wherein the input array, the separation array and the output array each comprise at least one digital microfluidic element, the device further comprising a substantially non-polar liquid retained over the separation array, the method comprising the steps of:

a) drying the biological sample at a sample reservoir in fluid communication with the input array;

b) adding a volume of lysing liquid to a reservoir in fluid communication with the input array and actuating the device to transport the volume of lysing liquid to the sample reservoir, and drying the lysing liquid at the sample reservoir;

c) adding a volume of polar liquid to a reservoir in fluid communication with the input array and actuating the device to transport the volume of polar liquid to the sample reservoir, thereby obtaining a solution in which the hormone is dissolved; and d) actuating the device to transport a droplet of the solution to the separation array, wherein a non-polar impurity is extracted from the droplet while maintaining the droplet as a distinct liquid phase within the substantially non-polar liquid; and e) actuating device to transport the droplet from the separation array to the output array.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which.

DETAILED DESCRIPTION OF THE INVENTION

Generally speaking, the systems described herein are directed to devices and methods for separating a species from a liquid using digital microfluidics. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to devices and methods for the extraction of hormones from a sample using digital microfluidics.

Figure 1:
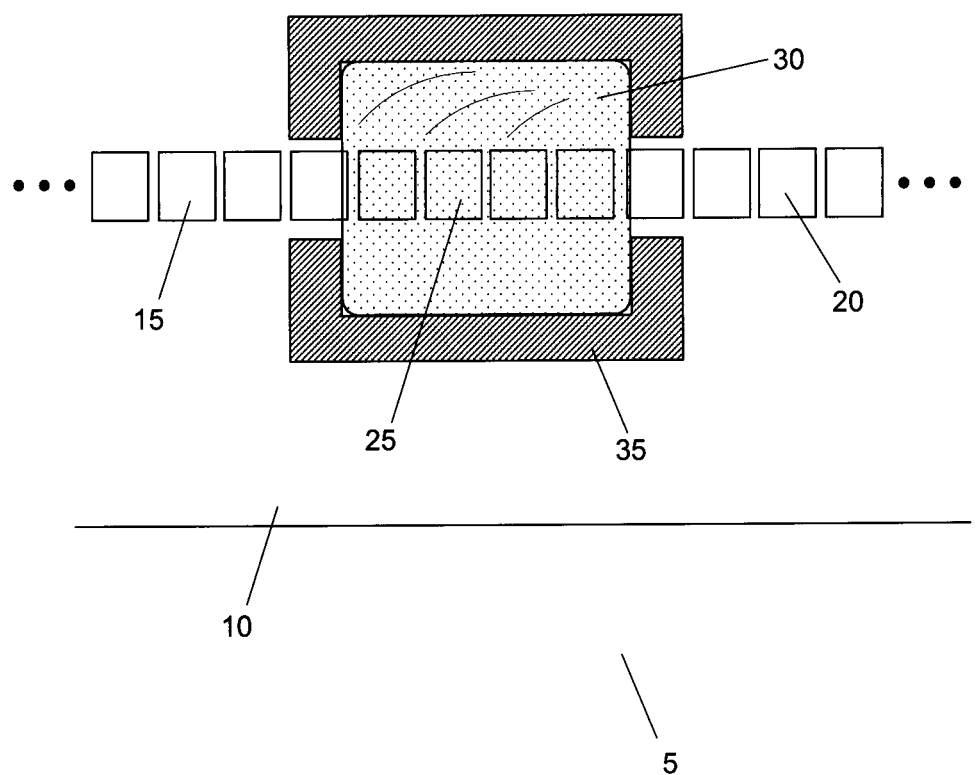
FIG. 1 illustrates a liquid-liquid separation device according to a preferred embodiment.

A first embodiment provides a device for liquid-liquid extraction of a species on a digital microfluidic array. FIG. 1 illustrates the digital microfluidic device 5, which comprises surface 10, onto which the array of electrodes are deposited and subsequently coated with a hydrophobic insulator, thereby forming digital microfluidic array elements. The hydrophobic insulator is commonly Teflon-AF. Electrical contact pads (not shown) are connected to the individual electrodes, enabling the electrodes to be individually addressed. Such contact pads are preferably addressed by a controller, such as a computer, for coordinating the motion of droplets on the array. The electrodes are arranged adjacent to each other in a plane to form a path over which fluid can be transported. The path may be one-dimensional (as shown) or two-dimensional. Sample and reagent reservoirs (not shown) are preferably incorporated into the array by including electrodes that are capable of supporting more than one unit droplet of fluid. Unit droplets can be extracted from reservoirs by actuating an electrode adjacent to the reservoir.

Referring again to FIG. 1, the digital microfluidic array is shown further comprising an input array 15, and output array 20, and a separation array 25. Actuation of the input array enables the delivery of a liquid droplet to the separation array 25, and actuation of the output array enables the delivery of a liquid droplet from the separation array 25 to the output array.

As shown in FIG. 1, a substantially non-polar liquid 30 is provided over the separation array 25. The non-polar liquid is preferably retained by a liquid retaining means, such as boundary wall 35 that partially encloses separation array 25 without impeding the entrance and exit of droplets from the input and output array, respectively. Those skilled in the art will appreciate that a variety of retaining means may be employed, such as, but not limited to, surface tension, a change in the surface chemistry or surface texture, surface patterning, and a recessed region forming a shallow well area. In one embodiment, a shallow well may be formed having a depth that increases relative to the distance from the input and output apertures, enabling a smooth transition for droplets actuated by the array electrodes.

The device operates by actuating the electrodes of the input array 15 to transfer a droplet comprising a substantially polar liquid to the separation array 25. Due to the difference in the polarity between the droplet and the substantially non-polar liquid 30 retained over the separation array, the droplet may be actuated and transferred within the solvent while maintaining a distinct phase. Accordingly, the droplet may be further transferred out of the separation zone by array actuation, and transported onto the output array 20, for example, for further processing or use.

The device may be used for the separation of a non-polar species from a droplet into the substantially non-polar liquid. In a preferred embodiment, the device enables the purification of a droplet by extracting a non-polar species or cross-reactant into the substantially non-polar liquid. This preferred embodiment is discussed in further detail below with reference to an exemplary yet non-limiting hormone purification method and device.

During a separation or purification step, the separation array is preferably actuated to circulate the droplet relative to the retained liquid to improve the separation efficiency. FIG. 1 illustrates an embodiment involving a linear separation array, which in which the circulation may be achieved by a varying the direction of droplet motion. It is to be understood that a wide variety of array configurations are possible for the separation array, for example, configurations enabling the circulation of the droplet in a two-dimensional path. In another embodiment, the separation array may be sufficiently large to enable the parallel separation from two or more droplets.

The device and methods can be extended for the extraction of other analytes (i.e., peptides, amino acids, DNA, RNA, metals, drugs, hormones, and proteins) using the combination of various solvents (i.e., phenol, cyclohexane, hexane, chloroform, isooctane, methanol, diethyl ether, dichloromethane, ethyl acetate, acetone, methanol, isopropanol, acetonitrile, acetic acid, and water).

While the preceding embodiments have been disclosed in the context of an open digital microfluidic platform, the device may alternatively comprise a closed array. In a closed digital microfluidic array, a second planar surface, onto which a single planar electrode is typically deposited and subsequently coated with a layer of a hydrophobic insulator, is placed parallel to the first planar surface, forming a planar air gap. Fluid droplets placed on the array elements (i.e. on the insulating layer directly above an array electrode) can be made to move by applying a voltage between an array electrode and the single planar electrode. Alternatively, an open digital microfluidic array can be formed with the first surface alone, where droplets are moved by applying a voltage between neighbouring electrodes.

In one embodiment, the method of the invention is performed with a closed digital microfluidic array as described above. The electrodes are preferably square in shape with sides having a length of about 1 to 2 µm, and more preferably 1.5 µm. Accordingly, the array electrodes are preferably able to transport unit droplets with a volume in the range of about 200-400 nl. The spacing between electrodes is preferably in the range of about 20-60 µm, and more preferably about 40 µm. The gap between the upper and lower planes of the closed digital microfluidic array is preferably in the range of about 50-250 µm, and more preferably about 100 µm. However, the method can be performed with a wider range of droplet volumes, for example, 10 picoliters to 3 mL. Likewise, the size and dimension of the electrode can vary depending on each application.

In an exemplary but non-limiting embodiment, a method of extracting hormones from biological sample is provided using a digital microfluidic array, where the biological sample take on a wide range of forms, including, but not limited to, blood, blood, serum, plasma, urine and tissue. Advantageously, selected embodiments do not rely on large sample volumes and detectable hormone levels may be efficiently extracted from sample volumes of 1 µL or lower.

Figure 2:
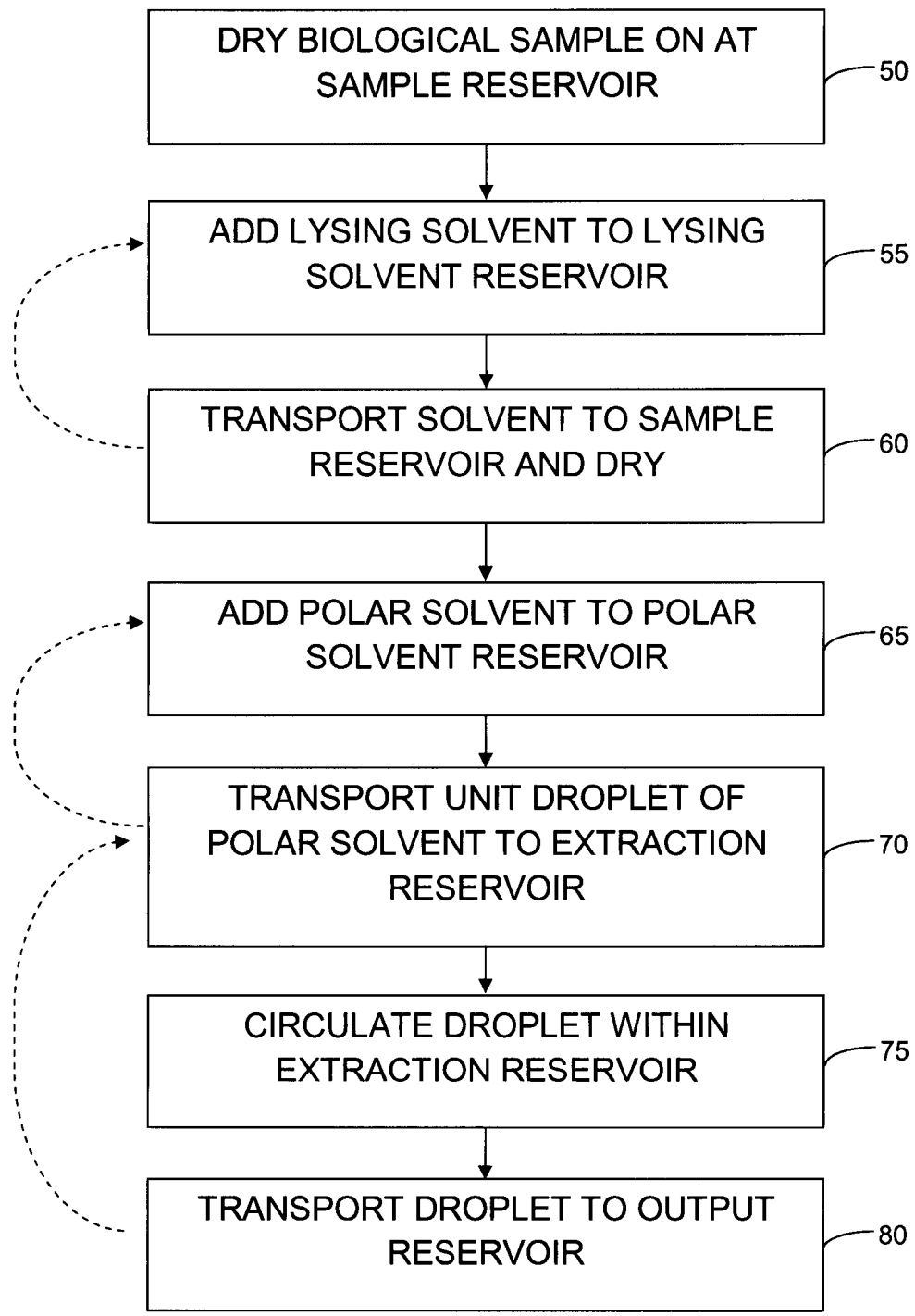
FIG. 2 shows a flow chart describing a method of extracting a hormone from a biological sample using a digital microfluidic (DMF) device.

The main steps of the method are provided in the flowchart shown in FIG. 2. The method is performed by drying and lysing a biological sample, extracting the hormones into a polar solvent, and purifying the solution of extracted hormone in polar solvent by moving droplets of the solution through a non-polar solvent. Fluidic transport is achieved using a digital microfluidic array to move individual droplets of fluid between reservoirs. The flowchart in FIG. 2 is described in connection with FIG. 3, which illustrates a preferred embodiment of a digital microfluidic extraction device.

Figure 3:
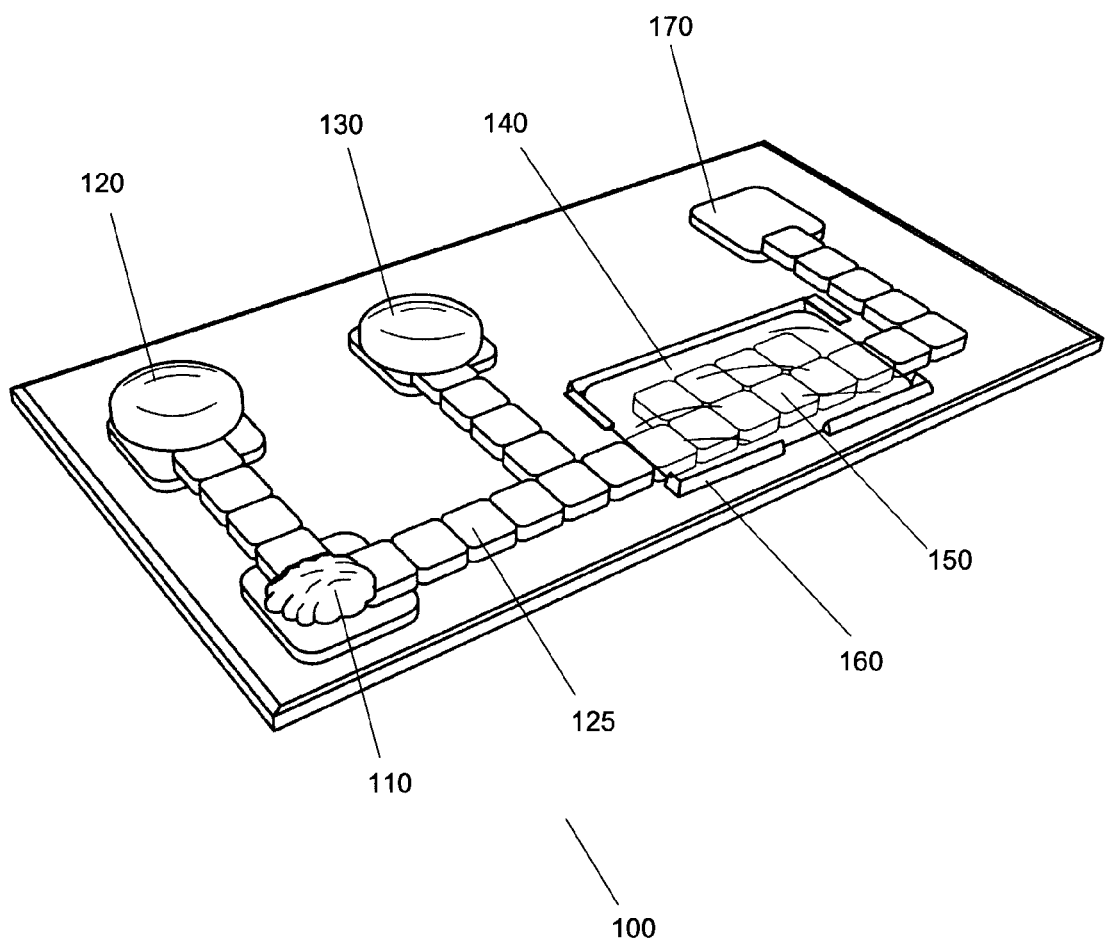
FIG. 3 provides a schematic of the DMF device, which includes sample and solvent reservoirs and the liquid-liquid separation zone.

Referring to FIG. 3, the device 100 preferably includes a sample reservoir 110 and one or more reagent reservoirs 120, 130. The reservoirs preferably support a volume greater than one unit droplet. In one embodiment, the reservoir electrodes are sufficiently large to accommodate a volume of about 1 µL of fluid. The array comprises a series of electrodes 125 forming a path for translating droplets.

As shown in the first step 50 of FIG. 2, sample is introduced to the microfluidic digital array and allowed to dry at the sample reservoir 110. As described above, the sample may be a liquid biological sample, or may be a tissue sample such as breast tissue. Preferably, the sample volume is in the microliter range, for example, 1-20 µL, and more preferably is about 1 µL, which is advantageously much lower than the sample volumes required by prior art sample preparation methods. Samples and reagents including solvents may be added to the array through multiple means, including the lateral opening between the two planar surfaces, or through access ports in the upper surface.

After the sample has dried, a lysing solvent is added to a reservoir 120 (as shown in FIG. 3) on the array in step 55. The array is actuated in step 60 by applying a voltage to transport the lysing solvent to the sample reservoir in order to lyse the dried sample. The array is preferably actuated so that lysing solvent is transported dropwise to the sample reservoir, until the lysing solvent at the lysing reservoir has been consumed. The lysing solvent is subsequently allowed to dry. In a preferred embodiment, this step of adding lysing solvent, transporting the lysing solvent to the sample reservoir, and drying the lysing solvent, is repeated one or more times to achieve efficient lysing of the sample (as indicated by the dashed arrow in FIG. 2).

Although many sample matrixes require lysing of cells, the extraction of hormones from certain matrices, such as urine, plasma and serum, may not require a lysing step. Accordingly, an embodiment of the present invention does not require the aforementioned lysing step for sample matrices that do not contain significant amounts of biological cells. Alternatively, the lysing step may be carried out in a separate process step prior to performing the extraction method.

A volume of polar solvent is then added to a reservoir 130 (FIG. 3) on the array in step 65. The reservoir may be a dedicated reservoir for the polar solvent, or may be the same reservoir as that used to dispense the lysing solvent in the preceding step of the method. The array is actuated to transport the polar solvent in a dropwise fashion to the sample reservoir. Once transported to the sample reservoir, the polar solvent solubilizes the hormones present in the dried sample, forming a polar solution containing solubilised hormones.

The method further involves a separation step in which non-polar contaminants are removed from the polar solution. This is achieved by passing droplets of the polar solution through a non-polar solvent shown at 140 in FIG. 3. The polar and non-polar solvents are preferably chosen to ensure that a droplet of polar solvent may pass through a volume of non-polar solvent while maintaining its droplet phase, thereby enabling the separation of non-polar contaminants into the non-polar solvent while maintaining a droplet form that can be addressed and transported by the digital microfluidic array.

Liquid-liquid extraction is obtained by solubilities in two different immiscible liquids. Polar solutes (for example, hormones) dissolve preferentially in the more polar solvent (for example, methanol) while non-polar solutes (contaminants) will dissolve in non-polar solvent. In a preferred embodiment, the non-polar solvent is added subsequent to the preceding step of adding the polar solvent to the array. In another embodiment, the non-polar solvent is added to the separation reservoir at substantially the same time that the polar solvent is added to the array.

In one embodiment, the lysing solvent is a solution of about 80% dichloromethane and about 20% acetone by volume. Alternatively, the polar solvent can be methanol, and the non-polar solvent can be 2,2,4-Trimethylpentane (isooctane), or any solvent with dielectric point less than about 15. However, embodiments as disclosed herein are not limited to particular use of the solvents. Instead, the solvents and their volumes can vary depending on the analyte of interest and the type of biological sample analyzed.

Accordingly, the digital microfluidic array further includes a separation reservoir comprising one or more electrodes 150. In a preferred embodiment, the separation reservoir includes multiple electrodes. Also, the separation reservoir preferably includes a wall 160 to contain a volume of the non-polar solvent within the vicinity of the electrodes, where the wall does not interrupt the transport of liquid droplets into and out of the separation reservoir. The wall need not form a contiguous boundary around the separation reservoir, but should occupy a sufficient portion of a perimeter around the separation reservoir to maintain the non-polar volume within the reservoir.

The separation of non-polar contaminants from the polar solution is therefore accomplished by transporting a droplet of the polar solution from the sample reservoir to the separation reservoir (step 70), where the presence of the non-polar solvent enables the separation of contaminants from the droplet. Subsequently, the droplet is transported to an output reservoir 170 in step 80 by actuation of the array. In a preferred embodiment, the droplet is circulated in step 75 within the separation reservoir (by actuation of the array) one or more times to further assist in the removal of contaminants, before being transported to the output reservoir. In one embodiment, the electrodes within the separation reservoir are arranged in a single row, as shown in FIG. 1. In another embodiment, the electrodes are arranged in multiple rows. It should be noted, however, that the electrodes can be arranged in any design and shape depending on application. This process of extracting contaminants from the polar solution is preferably repeated until the polar solution residing at the sample reservoir has been substantially depleted, as shown by the dashed arrow in FIG. 2. In a preferred embodiment, the process steps from the addition of the polar solvent to the transfer of all polar solution to the output reservoir are repeated one or more times to obtain optimal extraction of hormones.

In an alternative embodiment, the method may be performed using an open microfluidic array. When performing the inventive method using an open microfluidic array, method steps should be performed sufficiently rapidly to enable the transport, mixing, separation and solubilisation steps prior to the evaporation of reagents.

The hormones can be lipid hormones (for example, steroid hormones, sterol hormones and prostaglandins), amine derived hormones, peptide and protein hormones. The steroid hormones are selected from the group consisting of estrogens, androgens, progestagen, glucocorticoids and mineralocorticoids. According to one embodiment of the invention, the steroid hormone is sex steroid, preferably estrogen or testosterone. Estrogen includes estradiol, estrone, estriol, estrogen metabolites, phytoestrogens, synthetic estrogens (such as equilin, equilenin, ethinyl estradiol) and bio-identical estrogens. Preferably, estrogen is estradio. Embodiments of the invention may also be employed for the detection of synthetic substances, such as anabolic steroids, and therefore useful in a steroid test in athletes.

In a preferred embodiment, a method is also provided for the extraction and subsequent assaying of one or more hormones from a biological sample. The assay may be immunoassays such as ELISA, EIA, RIA, lateral flow and flow-through formats. Preferably, the assay method is mass spectroscopy, and more particularly is GC/MS, LC/MS, LC/MS/MS, MALDI-MS or MALDI-TOF.

In one embodiment, the extracted solution (after being transported to the output reservoir) may be dried, following which step an assay buffer prior may be added to solubilize the extracted hormones into a buffer that is preferable for performing an assay.

The assay may be used to measure the concentration of one or more hormones in the biological sample. The concentration of a given hormone in the biological sample can be obtained from the measured concentration of the hormone in the extracted solution (or assay buffer) by multiplying the concentration obtained from the assay by a factor equal to the ratio of a the volume of the extracted solution (or assay buffer) to the volume of biological sample.

Embodiments of the present invention will now be illustrated with the following non-limiting and exemplary example of extraction and detection of estrogen from µl samples, but it will be appreciated that embodiments of the invention are not limited to estrogen or the solvents, solutions being used for estrogen extraction.

The inventive method is compatible with a range of clinical samples, including tissue, blood, serum, urine, plasma, follicular fluid, endometrial fluid, pelvic fluid, semen and cerebrospinal fluid. The tissue can be breast tissue, endometrial tissue, ovarian tissue, vaginal tissue, testicular tissue, prostate tissue, adipose tissue, brain tissue, liver tissue, hair and skin.

Example: Extraction and Detection of Estrogen from µL Samples

Figure 4:
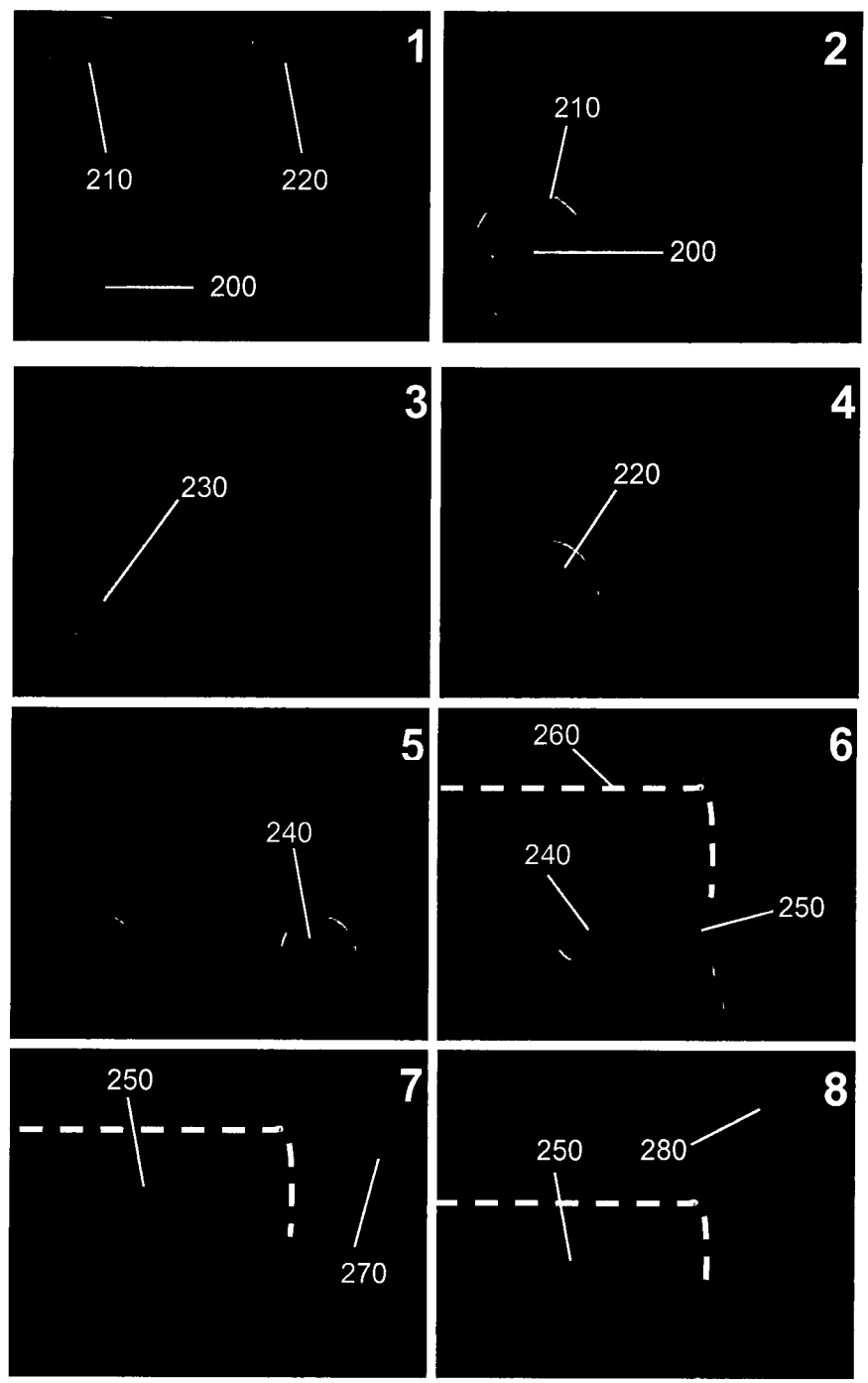
FIG. 4 shows a series of frames from a movie (1-8) illustrating the key steps in the DMF-based extraction of estrogen from a droplet of human blood (1 μL)

A digital microfluidic (DMF) device as illustrated in FIG. 3 was used for estrogen extraction. FIG. 4 shows a series of frames from a movie (1-8) illustrating the key steps in the DMF-based extraction of estrogen from a droplet of human blood (1 µL). As shown, a sample 200 is lysed with lysing solvent 210 and dried The estradiol is extracted into a polar solvent 220 (methanol). Subsequently, unwanted constituents are extracted from an estradiol-containing polar solvent droplet 240 into a non-polar solvent 250 (isooctane) bounded by a photoresist wall 260, and the purified solution 270 is delivered to a collection reservoir 280. Among the remarkable features of this technique is the ease with which the methanolic phase is separated from the isooctane phase after liquid-liquid separation (as shown in frame 7).

Device Fabrication

The digital microfluidic devices as illustrated in FIG. 3 were fabricated in the University of Toronto Emerging Communications Technology Institute (ECTI) clean room facility, using transparency photomasks printed at City Graphics (Toronto, ON). Glass wafers (Howard Glass Co. Inc., Worcester, Mass.) were cleaned in piranha solution (10 min), and coated with chromium (150 nm) by electron beam deposition (BOC Edwards, Wilmington, Mass.). After rinsing (acetone, methanol, DI water) and baking on a hot plate (115° C., 5 min), substrates were primed by spin-coating HMDS (3000 rpm, 30 s) and then spin-coating Shipley S1811 photoresist (3000 rpm, 30 s). Substrates were baked on a hot plate (100° C., 2 min) and exposed (35.5 mW/cm2, 4 s) through a transparency photomask using a Karl Suss MA6 mask aligner (Garching, Germany). Then substrates were developed (MF321 developer, 3 min) and postbaked on a hot plate (100° C., 1 min). After photolithography, exposed chromium was etched (CR-4, 2 min) and the remaining photoresist was stripped by sonicating in AZ300T (5 min).

After forming electrodes and cleaning in piranha solution (30 s), a photoresist wall was formed, using methods similar to those reported by Moon et al. [20]. Briefly, substrates were spin-coated with SU-8-25 (500 rpm, 5 s, then 1000 rpm, 30 s), baked on a hotplate (65° C., 5 min, then 95° C., 15 min), and then exposed to UV light (35.5 W/cm2, 7 s). After baking (65° C., 1 min, then 95° C., 4 min), and developing in SU-8 developer, substrates were coated with 2 µm of parylene-C and 100 nm of Teflon-AF. Parylene-C was applied using a vapor deposition instrument (Specialty Coating Systems, Indianapolis, Ind.) and Teflon-AF was spin-coated (1% by weight in Fluorinert FC-40, 1000 rpm, 1 min) followed by baking on a hot plate (160° C., 10 min). The polymer coatings were removed from contact pads by gentle scraping with a scalpel to facilitate electrical contact for droplet actuation. In addition to patterned devices, unpatterned indium-tin oxide (ITO) coated glass substrates (Delta Technologies Ltd, Stillwater, Minn.) were coated with Teflon-AF using the conditions described above.

The DMF device design of FIG. 3 included three input reservoir electrodes (3.5×3.5 mm) for the raw sample, lysing solvent, and polar extraction solvent, respectively, and a fourth reservoir electrode for collection of the processed sample. Actuation electrodes (1.5 mm×1.5 mm with a 40 µm inter-electrode gap) formed a path linking the input reservoirs, which passed through a fifth reservoir (delineated by a photoresist wall) containing non-polar solvent. Devices were assembled with an unpatterned ITO-glass top plate and a patterned bottom plate separated by a spacer formed from one or two pieces of double-sided tape (90 or 180 µm thick). Thus, depending on the spacer thickness, reservoir volumes were ~1.1 or 2.2 µL, and unit droplets (covering a single actuation electrode) were ~200 or 400 nL. A single spacer was used to process standard solutions of estradiol, while a double spacer was used for blood, serum, and tissue. Droplets were sandwiched between the two plates and actuated by applying AC potentials (18 kHz, 100 V) between the top electrode (ground) and sequential electrodes on the bottom plate via the exposed contact pads. Droplet motion was monitored by a CCD camera mated to an imaging lens positioned over the top of the device.

Further details of DMF devices and methods of construction and use of detectors associated therewith are disclosed in copending U.S. patent application Ser. No. 12/285,020 filed Sep. 26, 2008, U.S. patent application Ser. No. 12/285,567 filed Oct. 8, 2008, and U.S. Provisional Patent Application Ser. No. 61/136,896 filed Oct. 10, 2008, all of which are incorporated herein by reference in their entirety. These US patent references show various DMF devices and methods of manufacture.

As noted above, an array of separated electrodes which are independently activated by a controller, connects a series of reservoirs containing the sample and reagents. The process of estrogen extraction from a microliter of human blood is depicted in the movie frames of FIG. 4. As shown, in typical assays, samples were lysed, the estradiol was extracted into a polar solvent (methanol), unwanted constituents were extracted into a non-polar solvent (isooctane), and the purified solution was delivered to a collection reservoir. In addition to blood, the device and method illustrated in FIG. 3 is compatible with serum, breast tissue, and standard solutions, as described hereinafter.

Blood samples were collected from a healthy female volunteer on 5 different reproductive cycles (mid luteal phase). Serum was obtained by centrifugation of fresh blood samples at 800 RPM for 5 minutes, and both were kept at −20° C. until analysis. Breast tissue was obtained from apparently normal areas adjacent to breast cancer during surgery in two postmenopausal breast cancer patients and kept at −80° C. until analysis. Human ethics approvals were obtained from Mount Sinai Hospital and the Ontario Tumor Bank Research Ethics Boards (Toronto, Ontario, Canada).

Chemicals and Reagents

Dichloromethane (DCM) and 2,2,4-Trimethylpentane (Isooctane) 99.8% and HPLC-grade water were purchased from Sigma (Oakville, ON). Methyl alcohol (Methanol, HPLC grade) was from Fisher Scientific (Ottawa, ON). Estradiol (17-beta), Estrone, Testosterone and Androstenedione, deuterated Testosterone and deuterated androstenedione, were purchased from Steraloids Inc. (Newport, R.I.). Progesterone, Estriol, and 16-alpha-hydroxy estrone were purchased from Sigma (Oakville, ON). Deuterated progesterone was purchased from ICDN isotopes (Quebec, Canada). Estradiol EIA ELISA kits were from ALPCO Diagnostics (Salem, N.H.). Shipley S1811 photoresist and MF321 developer from Rohm and Haas (Marlborough, Mass.), AZ300T photoresist stripper from AZ Electronic Materials (Somerville, N.J.), parylene C dimer from Specialty Coating Systems (Indianapolis, Ind.), Teflon-AF from DuPont (Wilmington, Del.), solid chromium from Kurt J. Lesker Canada (Toronto, ON), CR-4 chromium etchant from Cyantek (Fremont, Calif.), hexamethyldisilazane (HMDS) from Shin-Etsu MicroSi (Phoenix, Ariz.), concentrated sulfuric acid and hydrogen peroxide (30%) from Fisher Scientific Canada (Ottawa, ON), Fluorinert FC-40 from Sigma (Oakville, ON), and SU-8 and SU-8 developer from MicroChem (Newton, Mass.). Piranha solution was prepared as a 3/1 v/v mixture of sulfuric acid/hydrogen peroxide.

Methodology of Digital Microfluidic (DMF) Estrogen Extraction

Two DMF-driven estrogen extraction techniques were developed; Method I, used in most experiments, comprised four steps. First, an aliquot of whole blood, serum, breast tissue homogenate, or estradiol standard solution was positioned in the sample reservoir of a device. The sample can be added to the device by pipetting, microchannel based capillary suction, direct sample deposition, paper/tissue absorption and microneedle.

Standard solutions were used immediately, and blood, serum, or tissue homogenate samples were allowed to dry to the surface. The top plate was then affixed and the solvents (DCM/acetone 80:20 v/v as lysing solvent, methanol as polar extracting solvent, and isooctane as non-polar extracting solvent) were loaded. Second, a series of reservoir volumes (9×1.1 µL or 5×2.2 µL) of DCM/acetone was dispensed and driven by DMF drop-wise to the sample, each of which was allowed to incubate until dry (~1 min per reservoir volume). Third, a reservoir volume of methanol (1.1 or 2.2 µL) was dispensed and driven by DMF to the dried lysate to dissolve the steroids. The dispensing can be carried out by, for example, pipetting.

It will be understood that the examples listed herein uses a limited list of solvents, but in general, depending on the extraction being undertaken, there is a broad spectrum of solvents, acids, alkalis and combination of solvents as well as solvent volumes that can be used according to the analyte of interest and the type of biological sample analyzed. Also, the arrangement of solvents in the reservoirs can be switched alternatively according to the polarity of the analyte of interest.

A unit droplet of the dissolved sample (200 or 400 nL) was dispensed and delivered by DMF to the isooctane reservoir and circulated within the pool (~20 s) prior to driving the droplet to the collection reservoir. This process was repeated until the sample reservoir was empty. Fourth, step three was repeated with successive reservoir volumes of methanol (for a total of 9×1.1 µL or 5×2.2 µL) to be sure to extract all of the free estradiol. Finally, all purified droplets were pooled in the output reservoir and allowed to dry.

In Method II, used to analyze percent recovery and experimental precision by ELISA, a standard solution of estradiol in methanol (1 µL) was positioned in the sample reservoir and the top plate was affixed (the lysis and polar solvent reservoirs remained empty). In each experiment, a single unit droplet (200 nL) of sample was dispensed, translated (and circulated) through isooctane, and delivered to the collection reservoir, all by DMF. The sample reservoir was then washed (manually) with methanol three times, and a fresh sample was positioned in the reservoir, and the process was repeated (twice), such that 3 purified droplets from replicate samples (i.e. ~600 nL total volume) were pooled in the collection reservoir and allowed to dry.

For all experiments, after collecting and drying the purified estrogenic solution, devices were stored at −20° C. Immediately prior to analysis, each extract was resolubilized in an aliquot (30 µL) of methanol/DCM (2:1 v/v), which was then dispensed into a small centrifuge tube. The solvent was then evaporated and the dry extract was reconstituted in a medium specific for the desired analysis.

Detection by Mass Spectrometry

Mass spectrometry was used to evaluate the performance of the DMF clean-up process in samples of whole blood or serum (obtained at two different days of the reproductive cycle). In each experiment, a 5 µL sample was dried and extracted by DMF (method one, as above), and the extract was reconstituted in 50 µL of methanol containing formic acid (0.1% v/v). Control (non-extracted) samples were prepared by drying and reconstituting 5-µL aliquots of blood or serum in 50 µL of methanol/formic acid (0.1% v/v), sonicating (10 min), and passing through a syringe filter (nylon membrane, 0.2 µm pore dia.). Samples were injected by nanoelectrospray into an LTQ Mass Spectrometer (Thermo Scientific, Waltman, Mass.) operating in the negative mode at 250° C. with a flow rate of 0.5 µL/min. Replicate spectra were obtained for DMF-extracted and control samples of both blood and serum.

Liquid chromatography and tandem mass spectrometry (LC-MS/MS) with multiple reaction monitoring (MRM) was used to evaluate estradiol in extracts from standard solutions, as well as in whole blood and breast tissue samples. Standard solutions (1 µL, 2 mg/mL in methanol) and blood (dried from 1 µL) were extracted by DMF (method one, as above) with no prior processing, while breast tissue (400 mg) was manually homogenized in DCM (1 mL), from which 1 µL samples were dried and processed similarly. In all cases, after extraction, samples were resuspended in 100 µL of methanol:water (20:80 v/v) and injected onto an HPLC (HP-Agilent 1100 series LC) interfaced by electrospray to a QTRAP LC-MS/MS (Applied Biosystems, Foster City, Calif.). The samples were analyzed in negative mode with multiple reaction monitoring, evaluating m/z 271 and 145 as an estradiol ion pair 21 to determine the extracted-ion current (XIC). Operating parameters included 300 µL/min flow rate, 4200 V spray potential, 60 collision energy and 400° C. temperature.

Detection by ELISA

An estradiol-specific ELISA was used (a) to evaluate the recovery and precision of the DMF method, and (b) to quantify estradiol in breast tissue samples. In these experiments, at least 3 replicate samples were evaluated for each condition by absorbance, measured at 450 nm using a µQuant microplate spectrophotometer (Bio-Tek, Instruments, Winooski, Vt.). The optical densities of samples and controls were compared with those of ELISA calibrator solutions using a standard curve to calculate estradiol concentrations as per the manufacturer's instructions.

For application (a), analysis of recovery and precision, the samples comprised serial dilutions of estradiol standard (500, 250, 100, and 3.3 ng/mL) in methanol. DMF-extracts of 3×1 µL samples were prepared using method two (as above), and for comparison, (non-extracted) control samples were prepared using the same procedure, but in devices lacking isooctane. After extraction, samples were resuspended in a 50-µL mixture of de-esterified serum (ALPCO Diagnostics) and methanol (4:1 v/v) and evaluated by ELISA. Recovery percentages were calculated as the inverse of the optical densities from extracted samples divided by those from non-extracted controls. For application (b), 1-µL samples of breast tissue homogenate (200 mg) in DCM (0.5 ml) from a breast cancer patient (a different patient than the one evaluated by MS) were processed manually (as above) and extracted by DMF using method one. The extricate was reconstituted in a 50-µL mixture of deestrified serum/methanol mixture (4:1 v/v) and was evaluated by ELISA.

DMF Extraction of Multiple Steroid Hormones

As described below, methods are provided for the use of a DMF chip to extract mixtures of multiple other steroid hormones. To achieve separation, devices and method as described in the aforementioned embodiments were used (the same extraction method was used as detailed above for estradiol). Two groups of hormones were studied. The first included a mix of Progesterone (P), Androstenedione (A) and Testosterone (T). The second included a mix of (Estrone (E1), Estradiol (E2), Estriol (E3) and 16-alpha-hydroxyestrone (16-alpha-OH-E1).

The detection and efficiency of extraction of the DMF was evaluated for a methanolic standard mix of progesterone, testosterone and androstenedione using nanoelectrospray into an LTQ Mass Spectrometer (Thermo Scientific, Waltman, Mass.) operating in the positive mode at 350° C. with a flow rate of 0.5 µL/min. The efficiency of extraction was calculated based on intensity relative to that of the deuterated internal standard of each analyte The detection of the DMF extracted four estrogenic hormones in a standard mix were evaluated by a NanoLC (Eksigent)/LTQ Mass Spectrometer operated in the negative mode at 260° C. The LC method included multiple reaction monitoring method for the four hormones as following (E1 m/z 269/145, E2 m/z 255/237, E3 m/z 287/269 and 16-alpha-OH-E1 m/z 285/213).

Results

Figure 5:
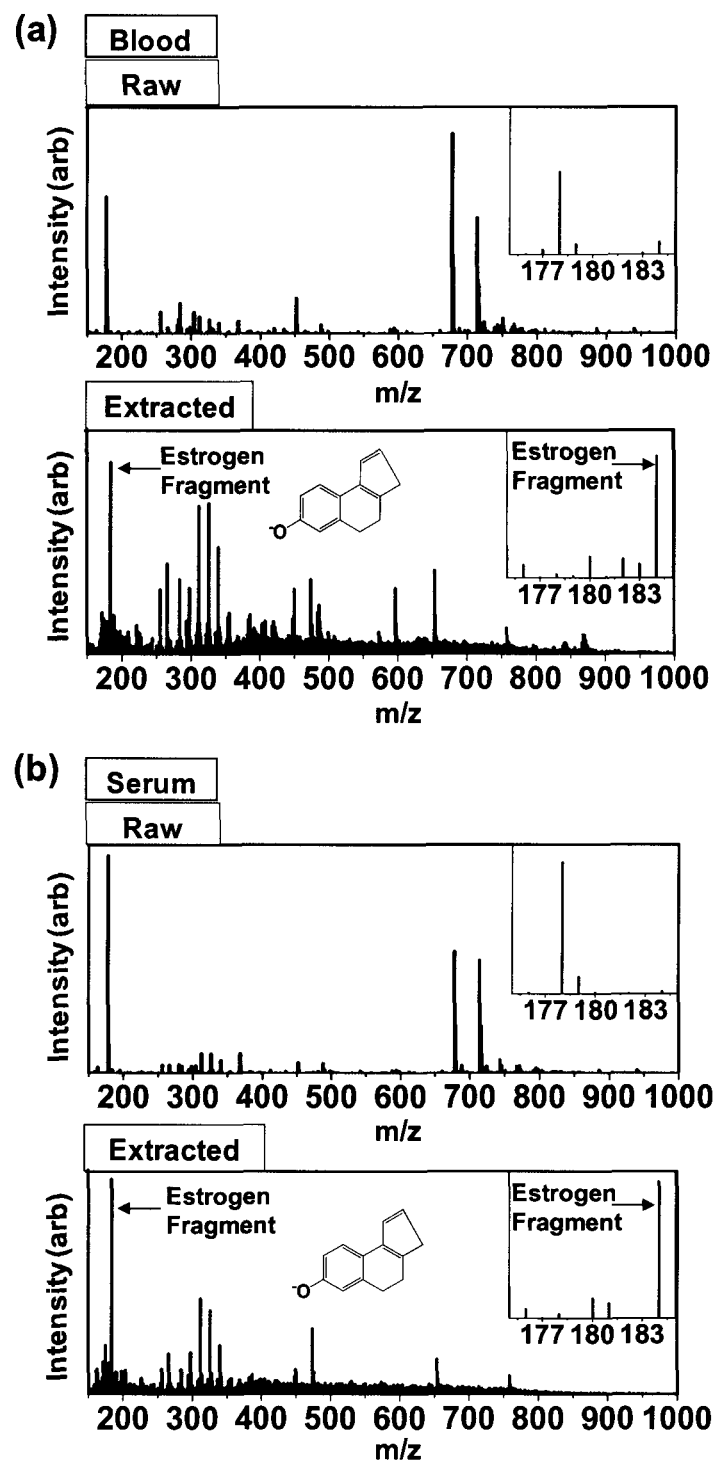
FIG. 5 shows mass spectra of raw and DMF-extracted samples, representative spectra generated from (a) blood and (b) serum obtained from a female volunteer at different days of the menstrual cycle in which the insets show that the estrogen fragment at m/z 183 is detected in extracted samples but not in raw samples.

As mentioned above, mass spectrometry was used to evaluate the efficacy of extraction by the digital microfluidic method. FIG. 5 contains representative spectra generated from raw samples and extracted samples of blood and serum obtained from a female volunteer at two different days of one reproductive cycle. Specifically, FIGS. 5(a) and (b) show the mass spectra of raw and DMF-extracted samples. Representative spectra generated from 2(a) blood and 2(b) serum obtained from a female volunteer at different days of the menstrual cycle. The insets show that the estrogen fragment at m/z 183 is detected in extracted samples but not in raw samples. In addition, several peaks of potential interferants, tentatively identified as fragments of tyrosine (m/z 178) DNA helicase (m/z 677), and porphyrin (m/z 715) are absent in the extracted samples, suggesting that their concentrations have been substantially reduced.

As shown, estradiol (m/z 183) was not detected in the spectra of raw samples, but was the peak of highest intensity in those from DMF-extracted samples. In addition, the intensities of peaks of potential interferants, tentatively identified as fragments of tyrosine [22] (m/z 178), DNA helicase (http://gpmdb.rockefeller.edu/) (m/z 677) [23] and porphyrin [24] (m/z 715), were suppressed in the spectra of extracted samples, indicating that their concentrations had been substantially reduced. These data highlight the importance of sample processing for this application—estradiol can only be ionized (and thus detected by mass spectrometry) after the many interfering compounds are removed [25].

Figure 6:
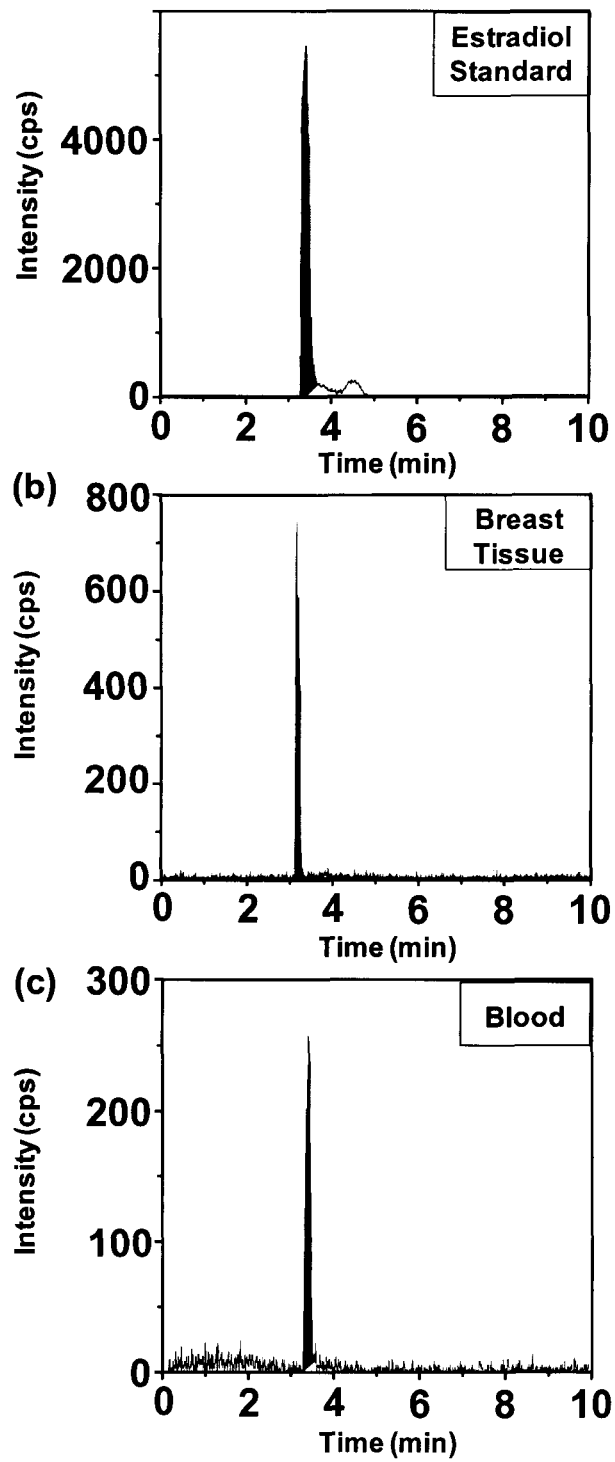
FIG. 6 shows LC-MS/MS analysis of DMF-extracted samples showing extracted-ion current (XIC) chromatograms generated by LC-MS/MS with multiple reaction monitoring from μL samples of (a) estradiol standard solution (2 mg/mL), (b) breast tissue of a postmenopausal patient with breast cancer, and (c) whole blood. The estradiol-specific ion pair evaluated for XIC was m/z 271/145.

FIGS. 6(a) to (c) show the LC-MS/MS analysis of DMF-extracted samples. Extracted-ion current (XIC) chromatograms were generated by LC-MS/MS with multiple reaction monitoring from µL samples of estradiol standard solution (2 mg/mL) (see FIG. 6(a)), breast tissue of a postmenopausal patient with breast cancer (see FIG. 6(b)), and whole blood (see FIG. 6(c)). The estradiol-specific ion pair evaluated for XIC was m/z 271/145. More specifically, to test the limits of the method disclosed herein for detecting estrogen in small samples, liquid chromatography and tandem mass spectrometry (LC-MS/MS) with multiple reaction monitoring (MRM) was used to evaluate estradiol extracted by DMF from standard solutions (FIG. 6(a)), breast tissue homogenate from a postmenopausal breast cancer patient (FIG. 6(b)) and whole blood from a female volunteer (FIG. 6(c)). As shown, estradiol was detected with high signal-to-noise ratio (S/N) at retention time ~3.2 min for all cases. Detection with high S/N in such tiny samples (1 μL) suggests that in the future, the new technique may be useful for non-invasive sex steroid testing.

Figure 7:
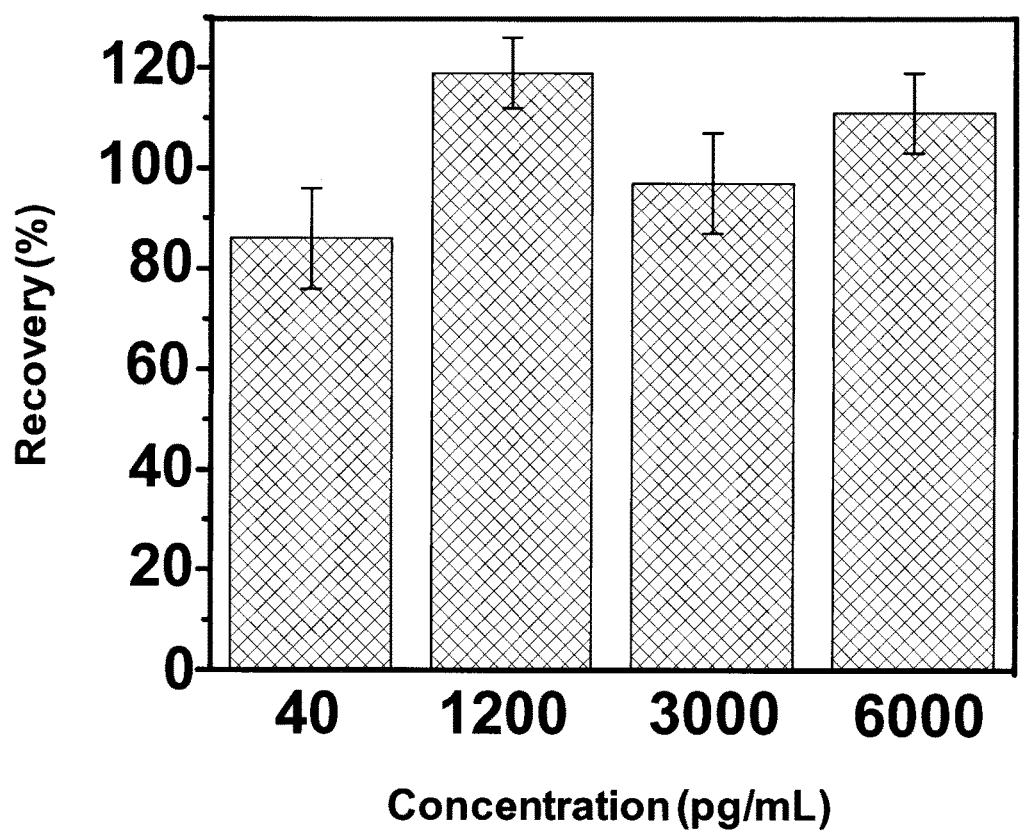
FIG. 7 shows plots of Recovery (%) versus concentration showing extraction efficiency analysis by ELISA, in which estradiol standards before and after extraction were evaluated by ELISA.

An absorbance-based ELISA was used to evaluate the compatibility of the new method with standard optical detection techniques. First, a method was developed for analyzing estradiol standards in a range of concentrations. FIG. 7 shows the extraction efficiency analysis by ELISA. Estradiol standards before and after extraction were evaluated by ELISA. As shown, extraction efficiencies from standard solutions (500, 250, 100, and 3.3 ng/mL) ranged from 86 to 119% with a CVs ranging from 7 to 10%. As shown in FIG. 7, the DMF-based extraction recoveries were high, ranging from 86 to 119% with CVs ranging from 7-10%. A similar method was then applied to analyzing extracts from breast tissue homogenate from a postmenopausal breast cancer patient. Replicate analyses of 1 μL samples (requiring ~20 min ea.) contained a mean concentration of 807 pg/mL estradiol. These data confirm that the new method disclosed herein is capable of robust, quantitative analyses of tiny volumes of clinically relevant samples.

Figure 8:
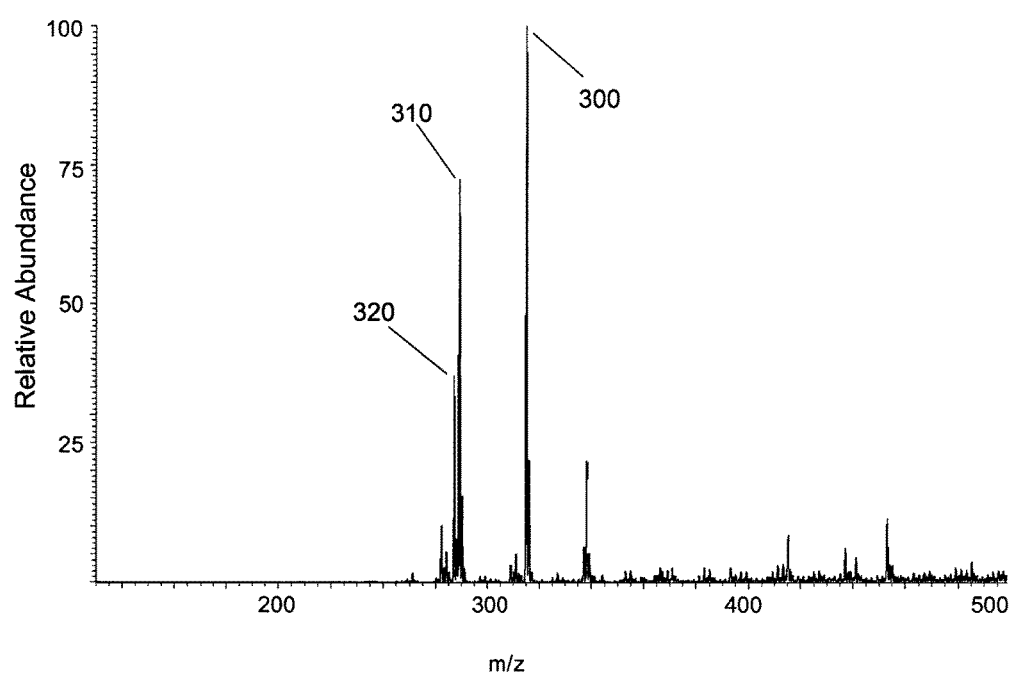
FIG. 8 shows mass spectra (MS1) of DMF extracted of 54 droplet of a standard mix of three steroid hormones including progesterone (m/z 315), testosterone (m/z 289) and androstenedione (m/z 287).

FIG. 8 shows mass spectra (MS1) of DMF extracted of 5 μL droplet of a standard mix of the three steroid hormones including progesterone (shown at 300, m/z 315), testosterone (shown at 310, m/z 289) and androstenedione (shown at 320, m/z 287).

Figure 9:
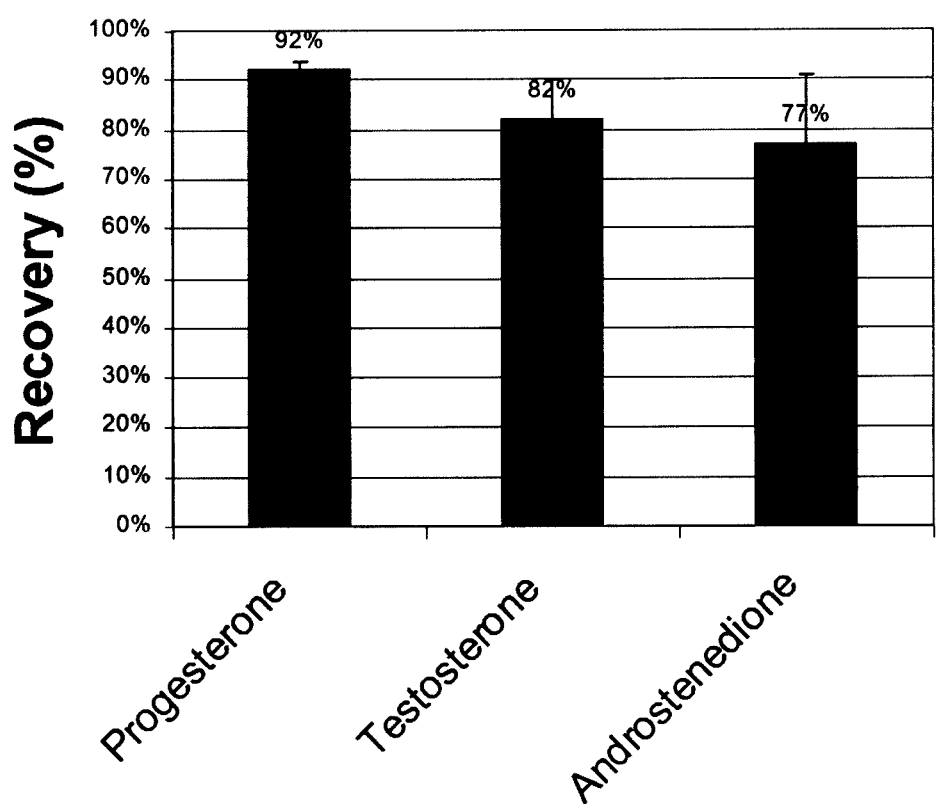
FIG. 9 shows plots of Recovery (%) representing the efficiency of extraction of the DMF for each of progesterone, testosterone and androstenedione. The efficiency of extraction was evaluated by mass spectrometry using deuterated internal standards for each analyte.

The efficiency of extraction of the DMF for each of progesterone, testosterone and androstenedione ranged between 77-92% with (2-14%) variations as shown in FIG. 9.

Figure 10:
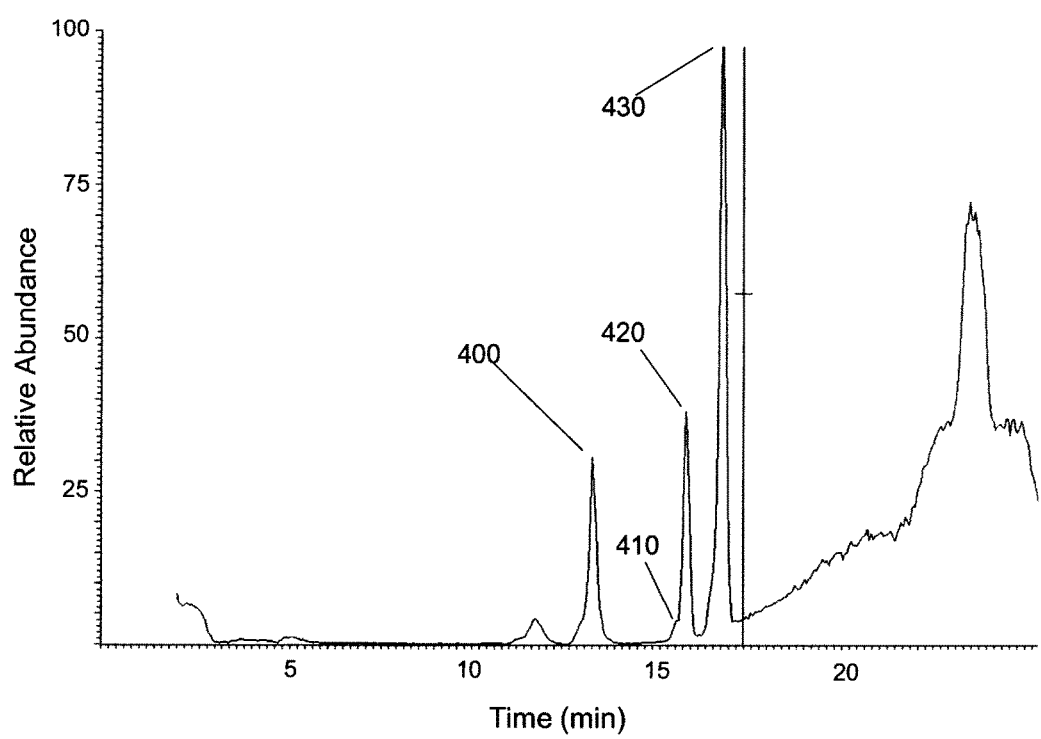
FIG. 10 shows the LC-MS/MS analysis of DMF-extracted 5 µL droplet mixture of multiple hormones showing total-ion count (TIC) chromatograms generated by LC-MS/MS with multiple reaction monitoring. The chromatogram peaks shows the extracted hormones including 16 alpha hydroxyl estrone (m/z 285), Estriol (m/z 287), Estradiol (m/z 271) and Estrone (m/z 269).

Total-ion count (TIC) chromatogram generated by LC-MS/MS with multiple reaction monitoring was able to show the DMF extracted four estrogenic hormones (E1, E2, E3, 16-alpha-OH-E1). The chromatogram peaks in FIG. 10 show the extracted hormones including 16 alpha hydroxyl estrone (shown at 400, m/z 285), Estriol (shown at 410, m/z 287), Estradiol (shown at 420, m/z 271) and Estrone (shown at 430, m/z 269).

Figure 11:
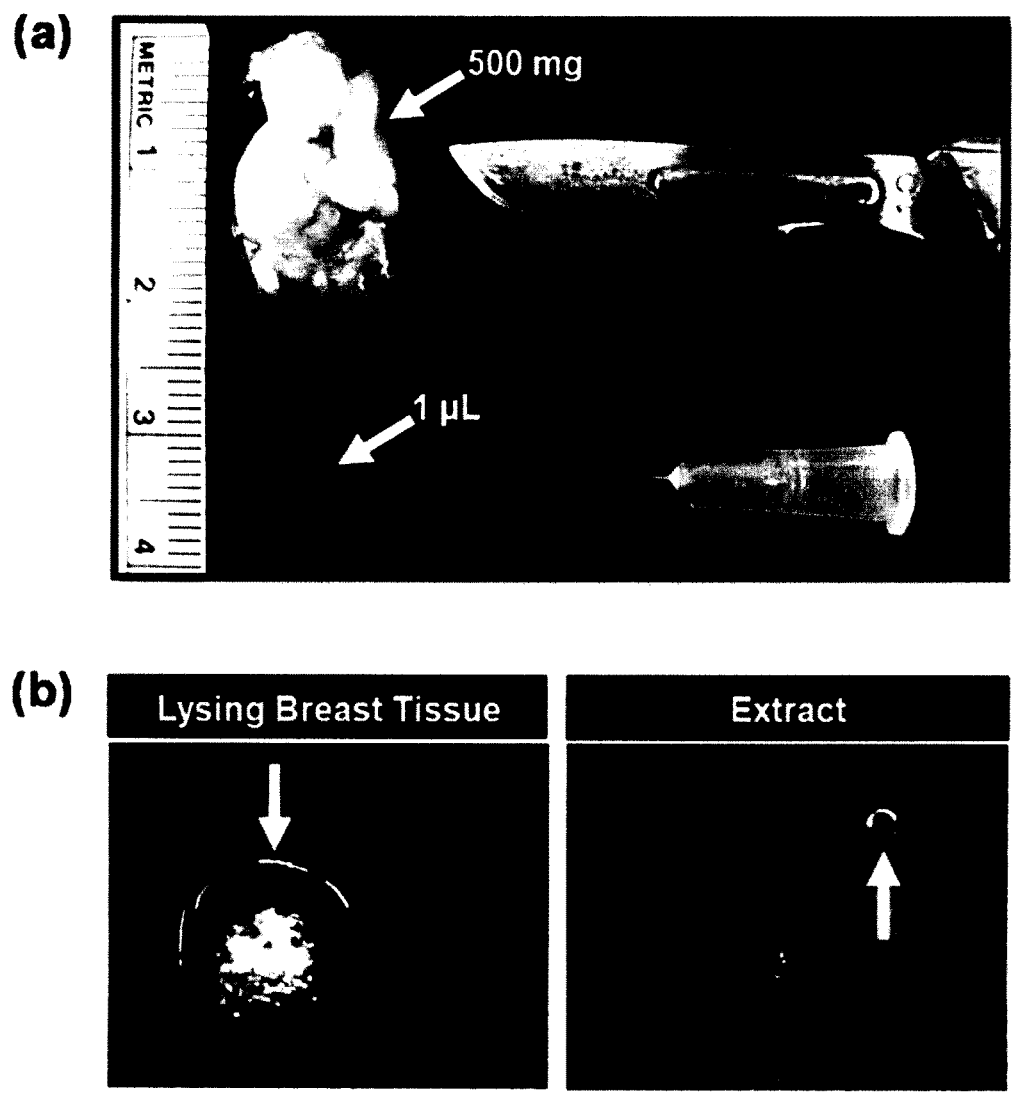
FIG. 11(a) is a picture of 500 mg of breast tissue collected by incisional biopsy (representing the sample size required for conventional analysis methods) compared to a 1 µL microaspirate collected using a 30 ga. needle (representing the sample size used with the new method), and (b) shows pictures of breast tissue microaspirate (1 µL) being lysed on the DMF device and of the dried estrogen extracted from it.

To the best of the inventors' knowledge, this is the first disclosure of a method for the extraction of steroids, hormones, sex hormones from microliter-sized clinical samples. These volumes are 500 times smaller than those required for conventional analysis methods [16, 17, 26-28]. FIG. 11(a) shows a picture of 500 mg of breast tissue collected by incisional biopsy (representing the sample size required for conventional analysis methods) compared to a 1 μL microaspirate collected using a 30 ga. needle (representing the sample size used with the new method). FIG. 11(b) shows pictures of breast tissue microaspirate (1 μL) being lysed on the DMF device and of the dried estrogen extracted from it.

As depicted in FIGS. 11(a) and (b), this substantial reduction in sample size may eventually result in drastically less-invasive collection procedures, facilitating routine testing of finger pricks of blood or microaspirates of tissue. The former (finger pricks) would facilitate improved patient compliance and clinical outcomes for a variety of applications related to women's health—for example, infertility patients could be monitored over the span of their menstrual or assisted-reproduction cycles, which would assist in proper timing of clinical interventions. The latter (tissue microaspirates) could have an even greater impact on women's health, as described below.

The new method reported here allows for the analysis of estrogen in tiny samples of homogenized breast tissue from menopausal breast cancer patients. It is now widely accepted that estrogen is a significant intracaine and paracrine factor (as opposed to a circulatory hormone) in many tissues including the breast [29-31]. Indeed, in situ biosynthesis of estrogen contributes up to 75% of the total estrogen produced in premenopausal women and almost 100% in menopausal women [29]. Thus, blood estrogen is not reflective of local concentrations inside the breast and may not be sufficient for identification of women with high risk for developing breast cancer, or to monitor the effect of anti-estrogen breast cancer therapies [32, 33]. While this is widely recognized, the measurement of local concentrations of estrogens is not common, because of the present requirement for a large tissue biopsy (which requires local anesthesia and carries the risk of scarring or deformity). Thus, the inventors believe that the digital microfluidic method reported here, which does not require large tissue biopsies (and is compatible with non-scarring, low-invasive microaspirate samples), has the potential to ushering in a new era of treatment and diagnosis of breast cancer relying on routine measurement of local tissue concentrations of estrogen.

In addition to the advantages arising from the use of smaller samples, the automation and integration in the digital microfluidic method makes it considerably less time- and labour-intensive relative to conventional techniques (e.g., no centrifuge is used and the pipetting and prolonged drying steps are almost eliminated). In its current form, samples were processed on DMF devices and then transferred to a more conventional format for analysis by mass spectrometry or ELISA. The former method (MS) is particularly attractive for laboratory testing. The ELISA method is attractive for point-of-care applications; devices and methods with on-chip estrogen quantitation according to embodiments described above are well suited for use in a wide variety of clinical environments.

An important feature of the methods and devices described above is integrated sample extraction and cleanup. These steps are needed for tissue samples, but for serum samples, there are several so-called "direct" immunoassay kits intended for use in raw (non-extracted) samples. Unfortunately, these tests have been characterized as being non-specific and inaccurate because of cross reactivity with other hormones, and consensus is building that sample clean-up is a prerequisite for accurate evaluation of human serum estrogens [10, 13, 34, 35] and other steroids. In fact, the CDC has stated publicly that direct immunoassays do not generate reliable results, especially for samples containing low concentrations of steroids [36]. Thus, it is anticipated that integrated sample cleanup methods described herein may prove useful for a wide range of clinically relevant applications.

The methods described herein are powered by digital microfluidics, a technology that has received less attention than the related technique of microchannel-based fluidics. While microchannels are well suited for many applications (e.g., electrophoresis and other separation modalities, in vitro culture and analysis of cells, etc.), it is expected that this format is a poor match for the application disclosed here. Indeed, in the few reports [37-39] of microchannel-powered methods for liquid-liquid separation (representing only one of a series of steps required for estrogen extraction from clinical samples) the techniques have been inherently limited by the challenge of separating and collecting one phase from the other after they have come into contact. In contrast, this process is straightforward in the method reported here (FIG. 1b, frame 7), and the precise control over different reagents [40], phases [41] and volumes [42] afforded by digital microfluidics makes it a near-perfect match for this application.

In summary, the foregoing example has disclosed a lab-on-a-chip powered by digital microfluidics for sample clean-up and extraction of estradiol in microliter-sized clinical samples. This method has significant potential for clinical applications in reproductive endocrinology and breast cancer.

The examples and embodiments described herein are for illustrative purposes only. Modifications or changes in light thereof will be suggested to persons skilled in the art and are to be included within the spirit and purview of this application.

As used herein, the terms "about", and "approximately" when used in conjunction with ranges of concentrations, temperatures or other physical or chemical properties or characteristics is meant to cover slight variations that may exist in the upper and lower limits of the ranges of properties/characteristics.

Also, as used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

As used herein, the coordinating conjunction "and/or" is meant to be a selection between a logical disjunction and a logical conjunction of the adjacent words, phrases, or clauses. Specifically, the phrase "X and/or Y" is meant to be interpreted as "one or both of X and Y" wherein X and Y are any word, phrase, or clause.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

1. Ehrmann, D. A. Polycystic ovary syndrome. New England Journal of Medicine 352 (2005).
2. Smith, S., Pfeifer, S. M. & Collins, J. A. Diagnosis and Management of Female Infertility. Journal of the American Medical Association 290, 1767-1770 (2003).
3. Henderson, B. E., Ross, R. & Bernstein, L. Estrogens as a cause of human cancer: the Richard and Hinda Rosenthal Foundation award lecture. Cancer Res 48, 246-253 (1988).
4. Kaaks, R. et al. Postmenopausal serum androgens, estrogens and breast cancer risk: The European prospective investigation into cancer and nutrition. Endocrine-Related Cancer 12, 1071-1082 (2005).
5. Pitt, F. A. & Brazier, J. Hormone replacement therapy for osteoporosis. Lancet 335, 978 (1990).
6. Szarewski, A. & Guillebaud, J. Contraception. Current state of the art. British Medical Journal 302, 1224-1226 (1991).
7. Djerassi, C. Chemical birth of the pill. American Journal of Obstetrics and Gynecology 194, 290-298 (2006).
8. Hertz, R. & Bailar 3rd, J. C. Estrogen-progestogen combinations for contraception. Journal of the American Medical Association 198, 1000-1006 (1966).
9. Cunningham, G. R. Testosterone replacement therapy for late-onset hypogonadism. Nature Clinical Practice Urology 3, 260-267 (2006).
10. Stanczyk, F. Z., Lee, J. S. & Santen, R. J. Standardization of Steroid Hormone Assays Why, How, and When? Cancer Epidemiol Biomarkers Prev 16, 1713-1719 (2007).
11. Albrecht, L. & Styne, D. Laboratory testing of gonadal steroids in children. Pediatric Endocrinology Reviews 5, 599-607 (2007).
12. Rahhal, S. N., Fuqua, J. S. & Lee, P. A. The impact of assay sensitivity in the assessment of diseases and disorders in children. Steroids 73, 1322-1327 (2008).
13. Ankarberg-Lindgren, C. & Norjavaara, E. A purification step prior to commercial sensitive immunoassay is necessary to achieve clinical usefulness when quantifying serum 17-estradiol in prepubertal children. Eur J Endocrinol 158, 117-124 (2008).
14. Belanger, C. et al. Omental and subcutaneous adipose tissue steroid levels in obese men. Steroids 71, 674-682 (2006).
15. Labrie, F. et al. Androgen glucuronides, instead of testosterone, as the new markers of androgenic activity in women. The Journal of Steroid Biochemistry and Molecular Biology 99, 182-188 (2006).
16. Szymczak, J., Milewicz, A., Thijssen, J. H. H., Blankenstein, M. A. & Daroszewski, J. Concentration of Sex Steroids in Adipose Tissue after Menopause. Steroids 63, 319-321 (1998).
17. Blankenstein, M. A. et al. Intratumoral levels of estrogens in breast cancer. J Steroid Biochem Mol Biol 69, 293-297 (1999).
18. Santen, R. J. et al. Superiority of gas chromatography/tandem mass spectrometry assay (GC/MS/MS) for estradiol for monitoring of aromatase inhibitor therapy. Steroids 72, 666-671 (2007).
19. Wheeler, A. R. CHEMISTRY: Putting Electrowetting to Work. Science 322, 539-540 (2008).
20. Moon, H., Wheeler, A. R., Garrell, R. L., Loo, J. A. & Kim, C. J. An integrated digital microfluidic chip for multiplexed proteomic sample preparation and analysis by MALDI-MS. Lab Chip 6, 1213-1219 (2006).
21. Gentili, A. et al. Analysis of free estrogens and their conjugates in sewage and river waters by solid-phase extraction then liquid chromatography-electrospray-tandem mass spectrometry. Chromatographia 56, 25-32 (2002).
22. Deng, C., Li, W. & Zhang, X. Rapid determination of amino acids in neonatal blood samples based on derivatization with isobutyl chloroformate followed by solid-phase microextraction and gas chromatography/mass spectrometry. Rapid Communications in Mass Spectrometry 18, 2558-2564 (2004).
23. Macromolecules, N.R.f.M.S.A.o.B. & University, a.R. 2009).

24. Danton, M. & Lim, C. K. Porphyrin profiles in blood, urine and faces by HPLC/electrospray ionization tandem mass spectrometry. Biomedical Chromatography 20, 612-621 (2006).
25. Jessome, L. L. & Volmer, D. A. Ion Suppression: A Major Concern in Mass Spectrometry. LC-GC North America 24, 498-510 (2006).
26. Chetrite, G. S., Cortes-Prieto, J. C., Philippe, J. C. & Pasqualini, J. R. Estradiol inhibits the estrone sulfatase activity in normal and cancerous human breast tissues. Journal of Steroid Biochemistry and Molecular Biology 104, 289-292 (2007).
27. Burstein, H. J. Aromatase inhibitor-associated arthralgia syndrome. Breast 16, 223-234 (2007).
28. Falk, R. T. et al. Measurement of Sex Steroid Hormones in Breast Adipocytes: Methods and Implications. Cancer Epidemiol Biomarkers Prev 17, 1891-1895 (2008).
29. Labrie, F. Intracrinology. Molecular and Cellular Endocrinology 78, C113-C118 (1991).
30. Sasano, H., Suzuki, T. & Harada, N. From Endocrinology to Intracrinology. Endocr Pathol 9, 9-20 (1998).
31. Simpson, E. R. et al. Estrogen—the Good, the Bad, and the Unexpected. Endocr Rev 26, 322-330 (2005).
32. Lamar, C. A. et al. Serum sex hormones and breast cancer risk factors in postmenopausal women. Cancer Epidemiol Biomarkers Prev 12, 380-383 (2003).
33. Beattie, M. S. et al. Endogenous sex hormones, breast cancer risk, and tamoxifen response: an ancillary study in the NSABP Breast Cancer Prevention Trial (P-1). J Natl Cancer Inst 98, 110-115 (2006).
34. Dibbelt, L., Von Postel, G. & Knuppen, R. Determination of natural and synthetic estrogens by radioimmunoassay (I). Comparison of direct and extraction methods for quantification of estrone in human serum. Clinical Laboratory 44, 137-143 (1998).
35. Diver, M. J. & Nisbet, J. A. Warning on plasma estradiol measurement. Lancet 2, 1097 (1987).
36. Cuzick, J. Chemoprevention of breast cancer. Women's Health 2, 853-861 (2006).
37. Kralj, J. G., Sahoo, H. R. & Jensen, K. F. Integrated continuous microfluidic liquid-liquid extraction. Lab on a Chip—Miniaturisation for Chemistry and Biology 7, 256-263 (2007).
38. Okubo, Y. et al. Liquid-liquid extraction for efficient synthesis and separation by utilizing micro spaces. Chemical Engineering Science 63, 4070-4077 (2008).
39. Znidarsic-Plazl, P. & Plazl, I. Steroid extraction in a microchannel system—mathematical modelling and experiments. Lab Chip 7, 883-889 (2007).
40. Chatterjee, D., Hetayothin, B., Wheeler, A. R., King, D. J. & Garrell, R. L. Droplet-based microfluidics with nonaqueous solvents and solutions. Lab Chip 6, 199-206 (2006).
41. Jebrail, M. J. & Wheeler, A. R. Digital microfluidic method for protein extraction by precipitation. Anal Chem 81, 330-335 (2009).
42. Abdelgawad, M., Freire, S. L. S., Yang, H. & Wheeler, A. R. All-terrain droplet actuation. Lab on a Chip—Miniaturisation for Chemistry and Biology 8, 672-677 (2008).

Therefore what is claimed is:

1. A closed digital microfluidic device for the separation of a non-polar species from a substantial polar droplet to a substantially non-polar liquid, said device comprising:
a first substrate;
an input array comprising at least two digital microfluidic electrodes, wherein said input array is formed on said first substrate;
a separation array in flow communication with said input array, said separation array comprising at least two digital microfluidic electrodes formed on said first substrate;
an output array in flow communication with said separation array, said output array comprising at least two digital microfluidic electrodes formed on said first substrate;
a second substrate provided in a spaced relationship with said first substrate such that a gap is formed therebetween, wherein said first substrate and said second substrate enclose a volume including said input array, said separation array, and said output array, and wherein said second substrate comprises at least one electrode, such that the substantially polar droplet is transportable among said input array, said separation array, and said output array while contacting said second substrate under the application of voltages between respective electrodes of said first substrate and said second substrate; and
a retaining wall for retaining a substantially non-polar liquid over said separation array, wherein said retaining wall is provided such that the substantially non-polar liquid is retained over said separation array without filling the entire volume enclosed by said first substrate and said second substrate, wherein said retaining wall encloses said separation array with a first opening for an inlet into the separation array and a second opening for an outlet out of the separation array.

2. The device according to claim 1 wherein the gap between the first substrate and the second substrate has a height in the range of about 50-250 μm.

3. The device according to claim 1 wherein said retaining wall comprises a raised portion of photoresist.

4. The device according to claim 1 wherein said digital microfluidic electrodes of the input array, separation array, and output array each are coated with a hydrophobic insulator.

5. The device according to claim 1 further comprising one or more reagent reservoirs, said reservoirs comprising a digital microfluidic electrode in flow communication with said input array.

6. The device according to claim 1 wherein said separation array comprises a single row of array of digital microfluidic electrodes.

7. The device according to claim 1 wherein said separation array comprises a two-dimensional array of digital microfluidic electrodes.

8. The device according to claim 1 wherein a spacing between said digital microfluidic electrodes of the input array, separation array, and output array is in the range of about 20-60 μm.

9. The device according to claim 1 wherein said digital microfluidic electrodes of the input array, separation array, and output array comprise substantially square electrodes having sides with a length in the range of about 1 to about 2 mm.

10. A method of separating a non-polar species from a substantially polar droplet using a digital microfluidic device, said method comprising the steps of:
providing a digital microfluidic device according to claim 1;
actuating said device to transport said droplet from said input array to said separation array, wherein said species is extracted from said droplet while maintaining said droplet as a distinct liquid phase within said substantially non-polar liquid; and actuating said device to transport said droplet from said separation array to said output array.

11. The method according to claim 10 wherein said step of actuating said device comprises applying a voltage between contacts connected to adjacent digital microfluidic elements to transport said droplet.

12. The method according to claim 10 wherein said non-polar liquid is retained by said retaining wall, said retaining wall surrounding a portion of said separation array, wherein said wall means does not interrupt a path of said droplet during said steps of transporting said droplet to said separation array and transporting said droplet to said output array.

13. The method according to claim 10 wherein at least one of any of said digital microfluidic electrodes each comprise an electrode coated with a hydrophobic insulator.

14. The method according to claim 10, said method further comprising actuating said device to circulate said droplet among said digital microfluidic electrodes of said separation array prior to said step of transporting said droplet from said separation array to said output array.

15. The method according to claim 14 wherein said droplet is circulated among said digital microfluidic electrodes of said separation array two or more times prior to said step transporting said droplet from said separation array to said output array.

16. The method according to claim 14 wherein said digital microfluidic electrodes of said separation array are arranged in a single row.

17. The method according to claim 14 wherein said array of elements comprises a two-dimensional digital microfluidic electrodes of said separation array.

18. The method according to claim 10 wherein said droplet comprises an analyte and wherein said species comprises an impurity, said method comprising purifying said analyte by extracting said species into said non-polar liquid.

19. The method according to claim 10 wherein said droplet comprises an analyte and wherein said species comprises a cross-reactant in an assay for said analyte, said method comprising isolating said analyte by extracting said species into said non-polar liquid.

20. The method according to claim 19 further comprising the step of performing said assay using said isolated analyte as a sample.

21. A method of extracting a polar solute from a biological sample using a digital microfluidic device, said method comprising the steps of:
a) providing a digital microfluidic device according to claim 1;
b) drying said biological sample at a sample reservoir in fluid communication with said input array;
c) adding a volume of lysing liquid to a reservoir in fluid communication with said input array and actuating said device to transport said volume of lysing liquid to said sample reservoir, and drying said lysing liquid at said sample reservoir;
d) adding a volume of polar liquid to a reservoir in fluid communication with said input array and actuating said device to transport said volume of polar liquid to said sample reservoir, thereby obtaining a solution in which said polar solute is dissolved; and
e) actuating said device to transport a droplet of said solution to said separation array, wherein a non-polar impurity is extracted from said droplet while maintaining said droplet as a distinct liquid phase within said substantially non-polar liquid; and
f) actuating device to transport said droplet from said separation array to said output array.

22. The method according to claim 21 further comprising the steps of repeating steps e) and f) until said solution has been substantially removed from said sample reservoir.

23. The method according to claim 21 wherein step c) is repeated one or more times.

24. The method according to claim 21 wherein steps (d)-(f) are repeated one or more times.

25. The method according to claim 21 wherein a volume of said biological sample is about 1 to about 20 µL.

26. The method according to claim 21 wherein said sample is added to said device by one of pipetting, microchannel based capillary suction, direct sample deposition, paper/tissue absorption and microneedle.

27. The method according to claim 21 wherein said lysing liquid is a solution of about 80% dichloromethane and about 20% acetone by volume.

28. The method according to claim 21 wherein said non-polar liquid comprises a liquid with a dielectric point less than about 15.

29. The method according to claim 21 wherein a volume of said droplet is in the range of about 10 picoliters to about 3 mL.

30. The method according to claim 21 wherein said volume of lysing liquid added to said reservoir is about 1 µL.

31. The method according to claim 21 wherein said volume of polar liquid added to said reservoir is about 1 µL.

32. The method according to claim 21 wherein said droplet transported to said output array is subsequently analyzed by an assay.

33. The method according to claim 32 wherein assay is an immunoassay selected from the group consisting of ELISA, EIA, RIA, lateral flow and flow-through, and magnetic immunoassay.

34. The method according to claim 32 wherein said assay is a mass analysis assay format selected from the group consisting of GC/MS, LC/MS, LC/MS/MS, MALDI-MS and MALDI-TOF, DESI-MS and IMS/MS.

35. The method according to claim 21 wherein said polar solute comprises a hormone.

36. The method according to claim 35 wherein said hormone is selected from the group consisting of lipid hormones, steroidal hormones, sterol hormones, prostaglandins, amine derived hormones, peptide and protein hormones.

37. The method according to claim 35 wherein said hormone comprises a steroid selected from the group consisting of estrogens, androgens, progestins, progestagens, glucocorticoids and mineralocorticoids.

38. The method according to claim 35 where said hormone comprises an estrogen selected from the group consisting of estradiol, estrone, estriol, estrogen metabolites, phytoestrogens, synthetic estrogens, equilin, equilenin, ethinyl estradiol, and bio-identical estrogens.

39. The method according to claim 38 wherein said polar liquid is methanol.

40. The method according to claim 38 wherein said non-polar liquid is 2,2,4-Trimethylpentane (isooctane).

41. The method according to claim 35 wherein said biological sample is selected from the group consisting of blood, serum, plasma, follicular fluid, endometrial fluid, pelvic fluid, semen, urine, cerebrospinal fluid, and tissue.

42. The method according to claim 41 wherein said tissue is selected from the group consisting of breast tissue, endometrial tissue, ovarian tissue, vaginal tissue, testicular tissue, prostate tissue, adipose tissue, brain tissue, liver tissue, hair and skin.

43. A closed digital microfluidic device for the separation of a non-polar species from a substantial polar droplet to a substantially non-polar liquid, said device comprising:
a first substrate;
at least one input digital microfluidic electrode formed on said first substrate;
a separation array in flow communication with said input digital microfluidic electrode, said separation array comprising at least two digital microfluidic electrodes formed on said first substrate;
at least one output digital microfluidic electrode in flow communication with said separation array, said output digital microfluidic electrode formed on said first substrate;
a second substrate provided in a spaced relationship with said first substrate such that a gap is formed therebetween, wherein said first substrate and said second substrate enclose a volume including said input digital microfluidic electrode, said separation array, and said output digital microfluidic electrode, and wherein said second substrate comprises at least one electrode, such that the substantially polar droplet is transportable among said input digital microfluidic electrode, said separation array, and said output digital microfluidic electrode while contacting said second substrate under the application of voltages between respective electrodes of said first substrate and said second substrate; and
a retaining wall for retaining a substantially non-polar liquid over said separation array, wherein said retaining wall is provided such that the substantially non-polar liquid is retained over said separation array without filling the entire volume enclosed by said first substrate and said second substrate, wherein said retaining wall encloses said separation array with a first opening for an inlet into the separation array and a second opening for an outlet out of the separation array.

* * * * *